United States Patent [19]
Nicholas et al.

[11] Patent Number: 5,868,761
[45] Date of Patent: Feb. 9, 1999

[54] SURGICAL CLIP APPLIER

[75] Inventors: David A. Nicholas, Trumbull; Frank C. Maffei, Shelton; Daniel E. Alesi, Sherman, all of Conn.

[73] Assignee: United States Surgical Corporation, Norwalk, Conn.

[21] Appl. No.: 698,430

[22] Filed: Aug. 15, 1996

Related U.S. Application Data

[63] Continuation-in-part of Ser. No. 311,049, Sep. 23, 1994, which is a continuation-in-part of Ser. No. 134,017, Oct. 8, 1993, which is a continuation-in-part of Ser. No. 959,201, Oct. 9, 1992.

[51] Int. Cl.$^6$ ................................................... A61B 17/10
[52] U.S. Cl. ........................... 606/143; 606/139; 606/142
[58] Field of Search ................................... 606/139, 142, 606/143, 151

[56] References Cited

U.S. PATENT DOCUMENTS

| | | |
|---|---|---|
| 2,968,041 | 1/1961 | Skold . |
| 3,152,336 | 10/1964 | Brady . |
| 3,232,089 | 2/1966 | Samuels et al. . |
| 3,646,801 | 3/1972 | Caroli . |
| 3,753,438 | 8/1973 | Wood et al. . |
| 3,777,538 | 12/1973 | Weatherly et al. . |
| 4,152,920 | 5/1979 | Green . |
| 4,201,314 | 5/1980 | Samuels et al. . |
| 4,202,480 | 5/1980 | Annett . |
| 4,242,902 | 1/1981 | Green . |
| 4,256,251 | 3/1981 | Moshofsky . |
| 4,296,751 | 10/1981 | Blake, III et al. . |
| 4,299,224 | 11/1981 | Noiles . |
| 4,316,468 | 2/1982 | Klieman et al. . |
| 4,317,535 | 3/1982 | Huftel et al. . |
| 4,325,376 | 4/1982 | Klieman et al. . |
| 4,372,316 | 2/1983 | Blake, III et al. . |
| 4,425,915 | 1/1984 | Ivanov . |
| 4,427,008 | 1/1984 | Transue . |
| 4,430,997 | 2/1984 | DiGiovanni et al. . |
| 4,448,193 | 5/1984 | Ivanov ..................................... 606/143 |
| 4,450,839 | 5/1984 | Transue ................................... 606/143 |
| 4,452,357 | 6/1984 | Klieman et al. . |
| 4,452,376 | 6/1984 | Klieman et al. . |
| 4,462,404 | 7/1984 | Schwarz et al. . |
| 4,471,780 | 9/1984 | Menges et al. . |
| 4,478,220 | 10/1984 | DiGiovanni et al. . |
| 4,480,640 | 11/1984 | Becht . |
| 4,480,641 | 11/1984 | Failla et al. . |
| 4,509,518 | 4/1985 | McGarry et al. . |
| 4,512,345 | 4/1985 | Green . |

(List continued on next page.)

FOREIGN PATENT DOCUMENTS

| | | |
|---|---|---|
| 0406724 | 1/1991 | European Pat. Off. . |
| 0469524 | 2/1992 | European Pat. Off. . |
| 0507537 | 10/1992 | European Pat. Off. . |
| 8801486 | 3/1988 | WIPO . |
| 9421181 | 9/1994 | WIPO . |

*Primary Examiner*—Michael Buiz
*Assistant Examiner*—Tina T. D. Pham

[57] ABSTRACT

A surgical clip applicator having a housing, a pair of handles pivotally connected to opposite sides of the housing, and a jaw blade assembly fixedly connected to the housing is provided. The jaw blade assembly includes a pair of jaws for receiving and deforming a clip therebetween and a clip carrier for supplying a series of clips to the jaws. A channel assembly is slidably mounted with respect to the housing and envelops the jaw blade assembly for camming the jaws closed upon closing of the handles. The clips are urged by a pusher bar which provides a biasing force to advance the clips to be retained by the jaws. A jaw clamp is provided to maintain the jaw assembly in abutting relation to a clip cover. The applicator housing is formed from a pair of housing half-sections that may be secured together using interlocking and/or snap-fit structure. The instrument may be used in conventional surgical procedures, or may be adapted for endoscopic and laparoscopic surgical procedures requiring the application of microsurgical clips.

20 Claims, 20 Drawing Sheets

U.S. PATENT DOCUMENTS

| | | |
|---|---|---|
| 4,522,207 | 6/1985 | Klieman et al. . |
| 4,532,925 | 8/1985 | Blake, III . |
| 4,549,544 | 10/1985 | Favaron . |
| 4,562,839 | 1/1986 | Blake, III et al. . |
| 4,565,199 | 1/1986 | Becht . |
| 4,572,183 | 2/1986 | Juska . |
| 4,576,166 | 3/1986 | Montgomery et al. . |
| 4,586,503 | 5/1986 | Kirsch et al. . |
| 4,598,711 | 7/1986 | Deniega . |
| 4,611,595 | 9/1986 | Klieman et al. . |
| 4,616,650 | 10/1986 | Green et al. . |
| 4,624,254 | 11/1986 | McGarry et al. . |
| 4,630,608 | 12/1986 | Arroyo . |
| 4,637,395 | 1/1987 | Caspar et al. . |
| 4,662,373 | 5/1987 | Montgomery et al. . |
| 4,674,504 | 6/1987 | Klieman et al. . |
| 4,712,549 | 12/1987 | Peters et al. . |
| 4,733,664 | 3/1988 | Kirsch et al. . |
| 4,850,355 | 7/1989 | Brooks et al. . |
| 4,929,240 | 5/1990 | Kirsch et al. . |
| 4,983,176 | 1/1991 | Cushman et al. . |
| 5,030,226 | 7/1991 | Green et al. . |
| 5,047,038 | 9/1991 | Peters et al. . |
| 5,049,152 | 9/1991 | Simon et al. . |
| 5,084,057 | 1/1992 | Green et al. . |
| 5,104,395 | 4/1992 | Thornton et al. . |
| 5,112,343 | 5/1992 | Thornton . |
| 5,122,150 | 6/1992 | Puig . |
| 5,156,609 | 10/1992 | Nakao et al. . |
| 5,171,247 | 12/1992 | Hughett et al. . |
| 5,171,249 | 12/1992 | Stefanchik et al. . |
| 5,207,692 | 5/1993 | Kraus et al. . |
| 5,211,649 | 5/1993 | Kohler et al. . |
| 5,246,450 | 9/1993 | Thornton et al. . |
| 5,282,806 | 2/1994 | Haber et al. . |
| 5,330,487 | 7/1994 | Thornton et al. . |
| 5,370,658 | 12/1994 | Scheller et al. . |
| 5,409,498 | 4/1995 | Braddock et al. . |
| 5,431,668 | 7/1995 | Burbank, III et al. . |
| 5,501,698 | 3/1996 | Roth et al. . |

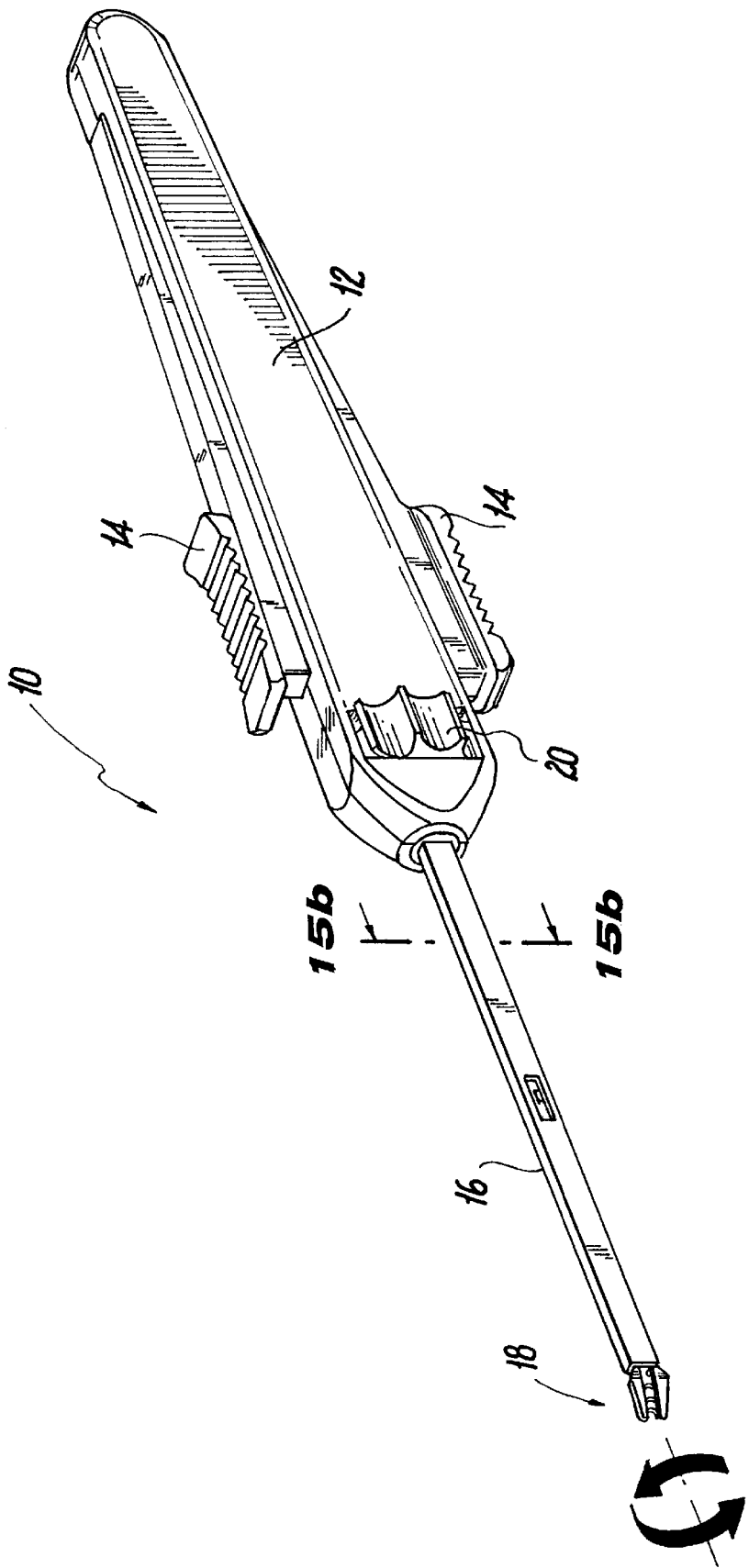

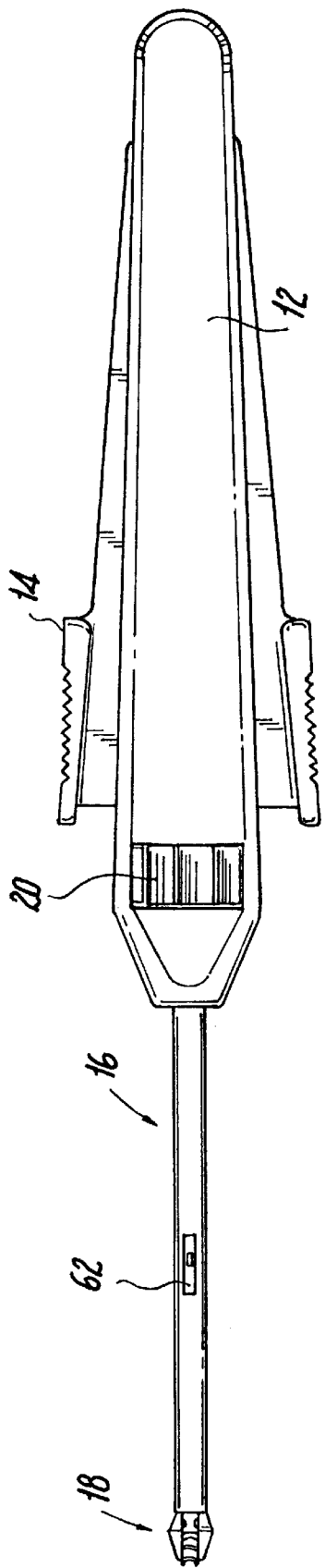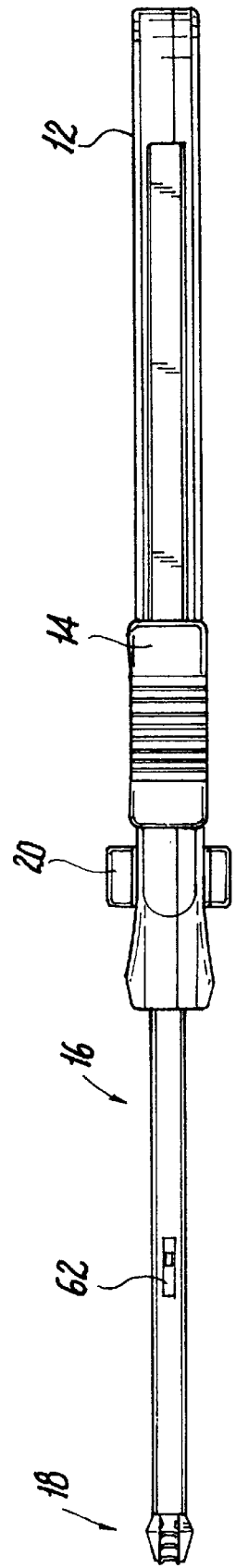

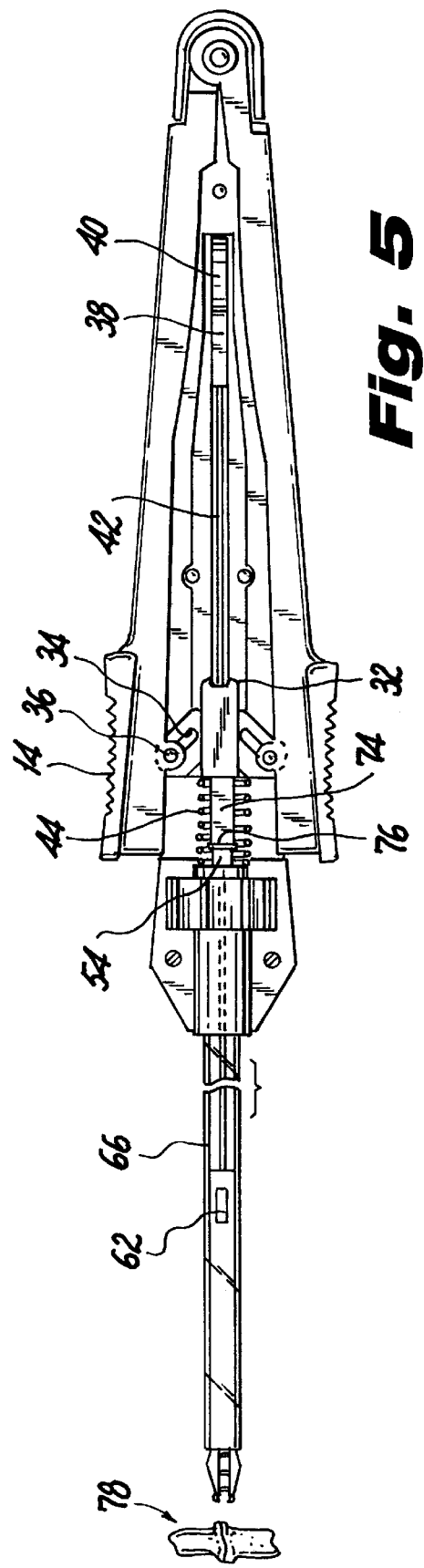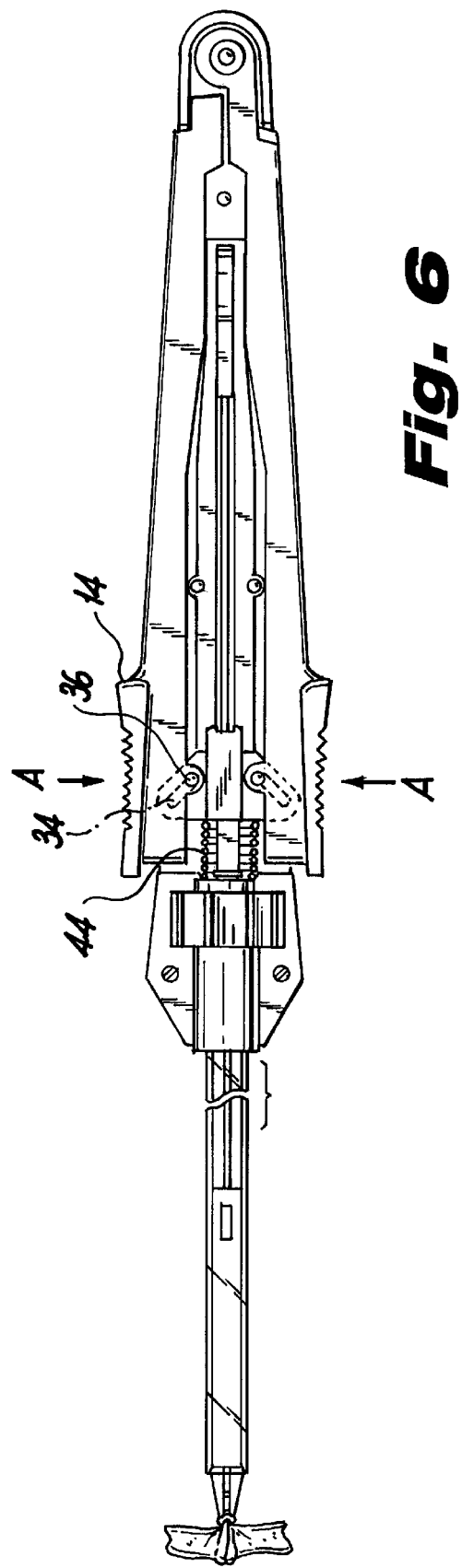

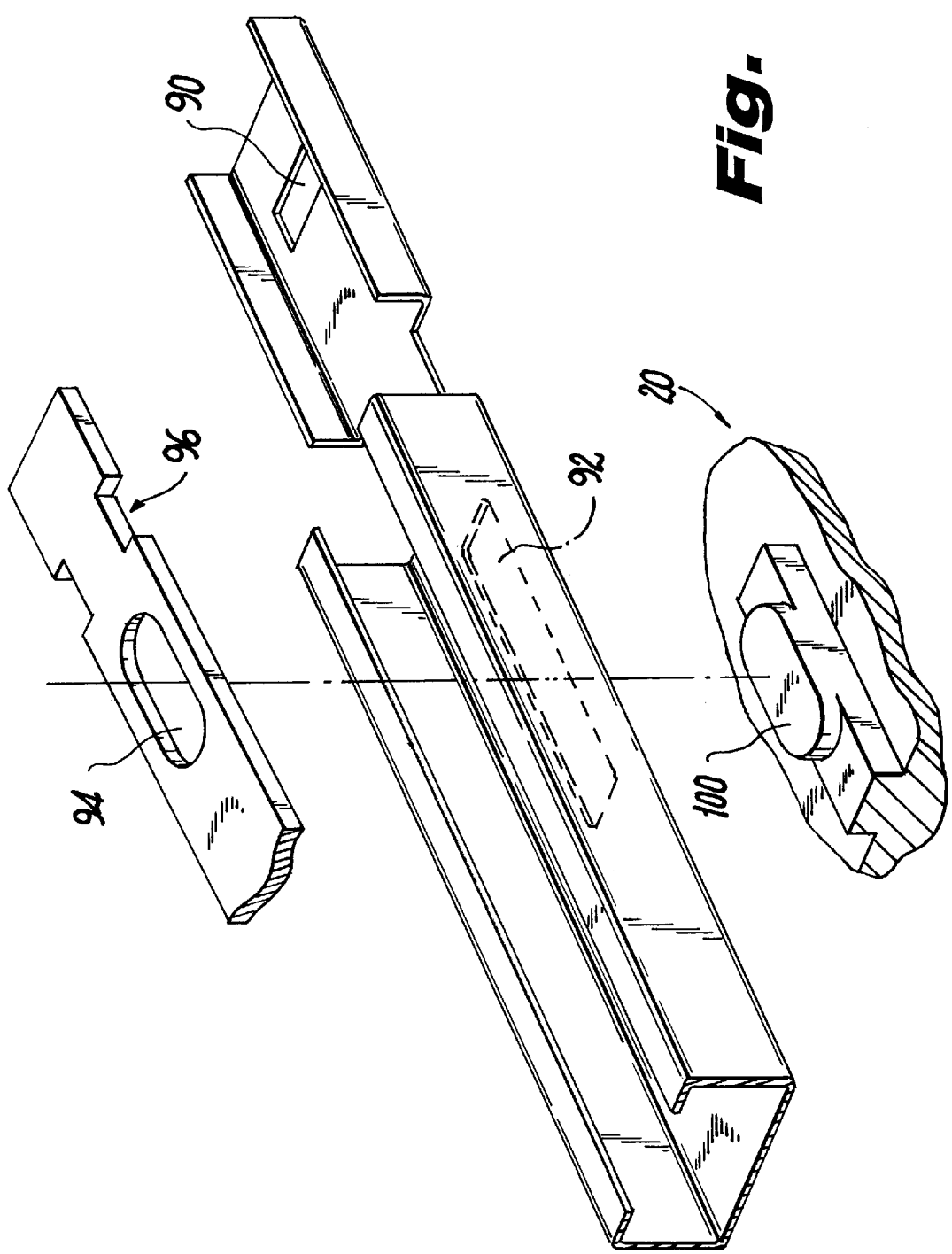

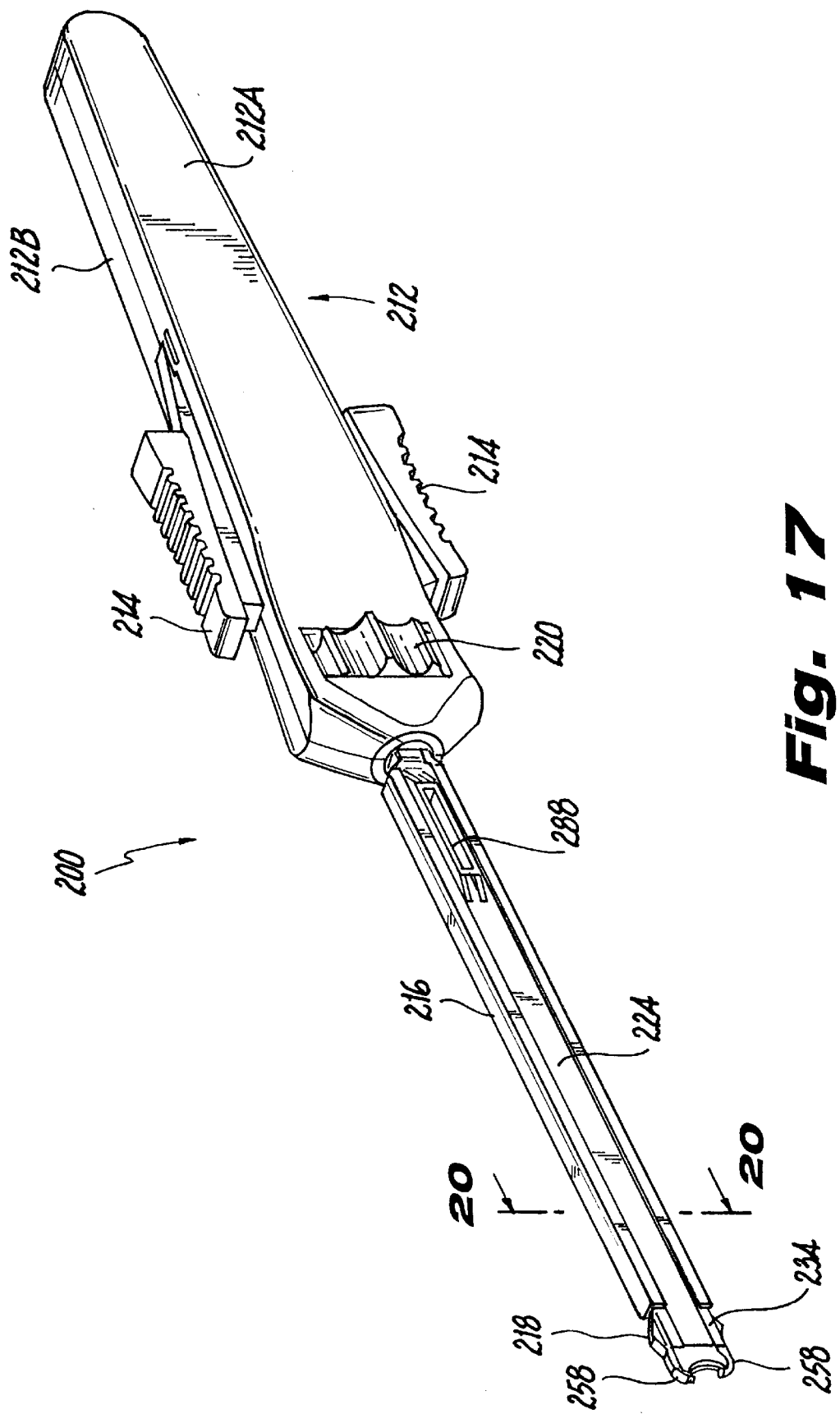

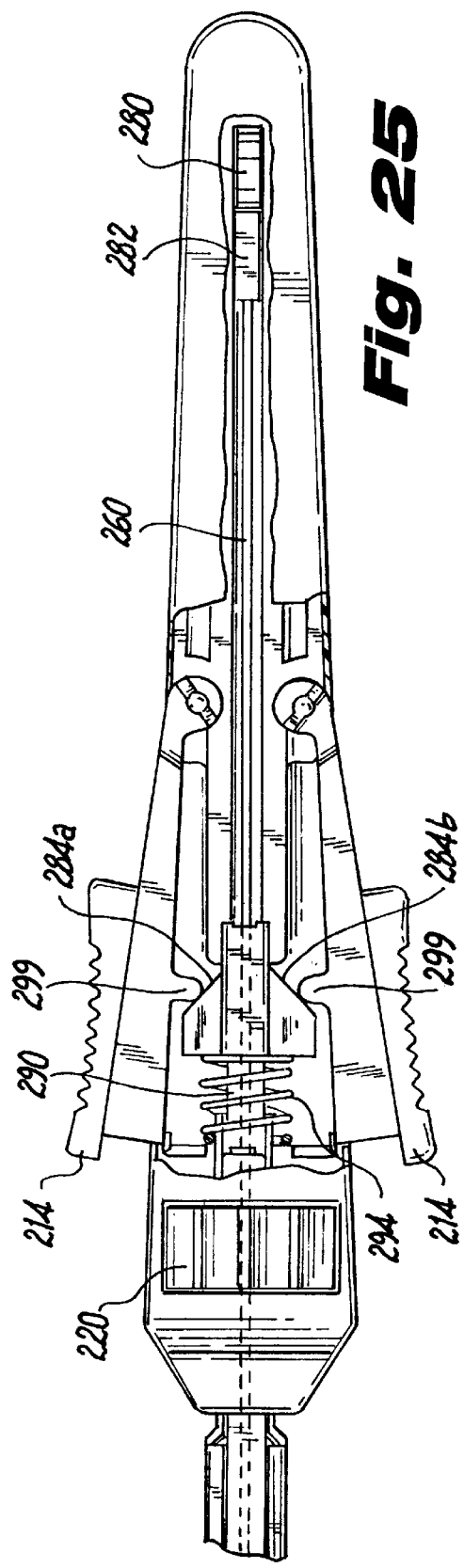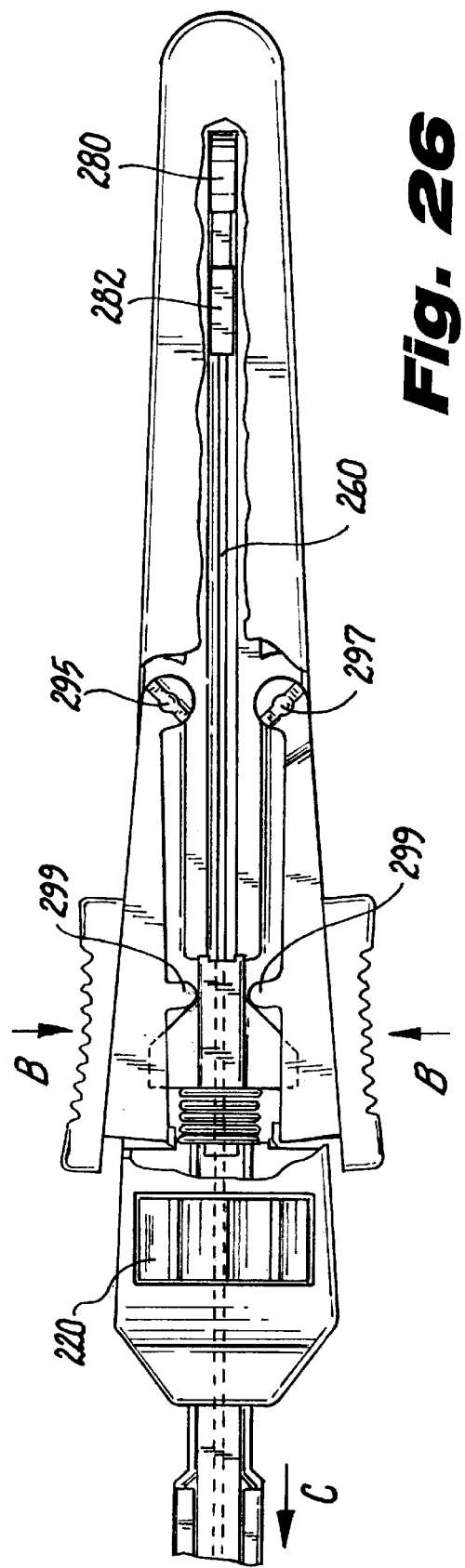

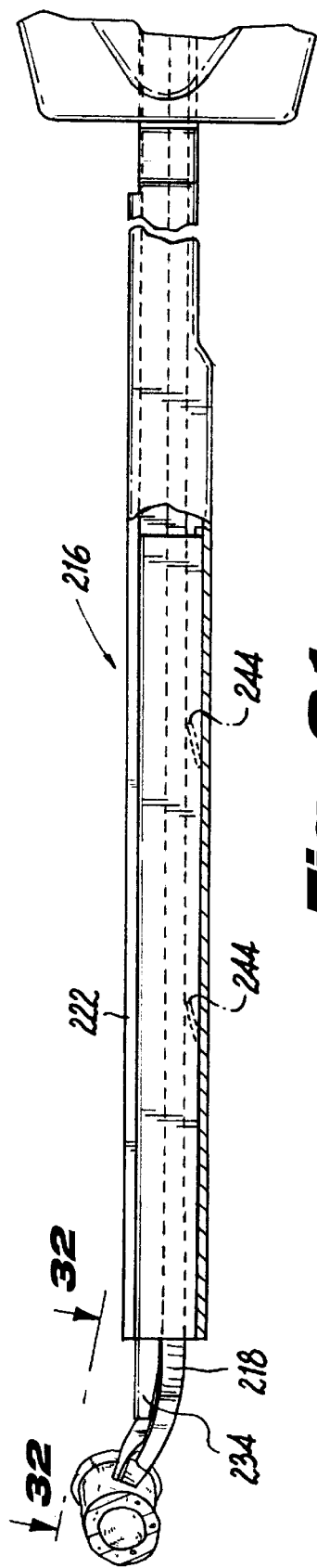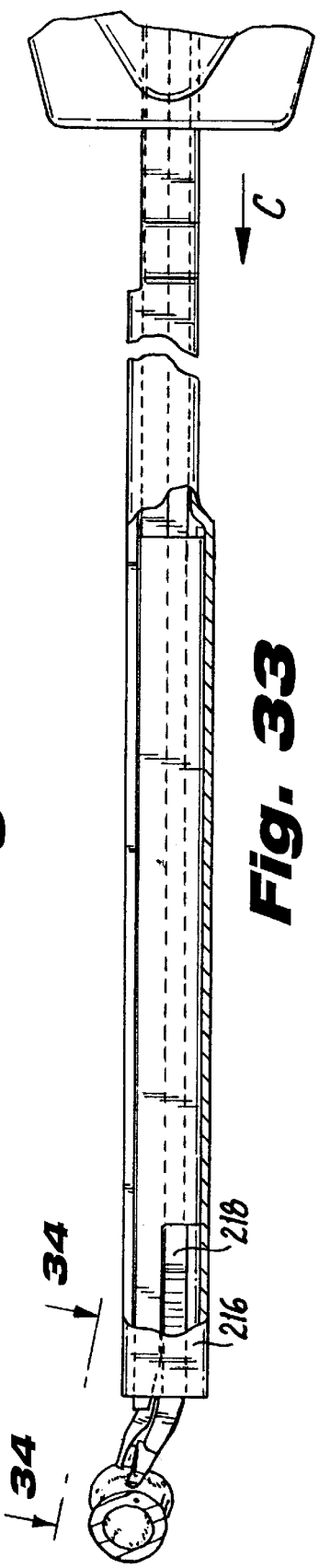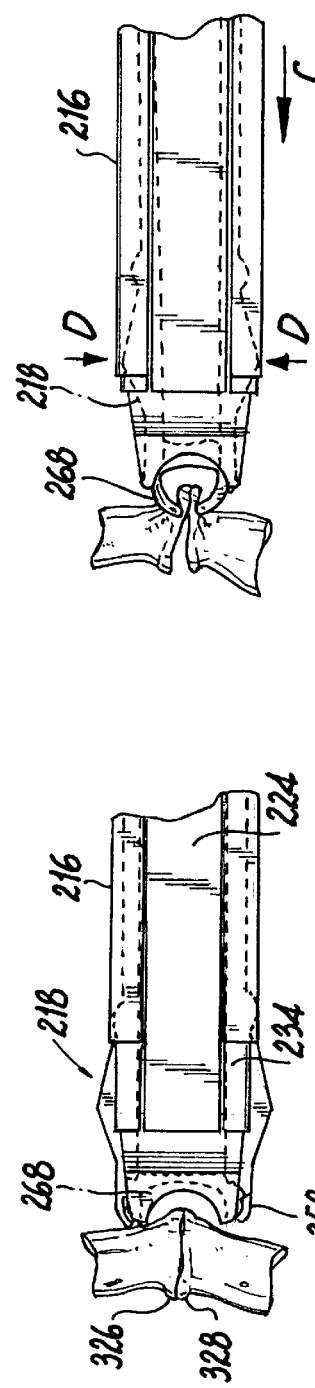

SURGICAL CLIP APPLIER

CROSS-REFERENCE TO RELATED APPLICATIONS

This application is a continuation-in-part of copending application Ser. No. 08/311,049, filed Sep. 23, 1994, which is a continuation-in-part of application Ser. No. 08/134,017, filed Oct. 8, 1993, which is a continuation-in-part of application Ser. No. 07/959,201, filed on Oct. 9, 1992. The contents of these applications are incorporated herein by reference.

BACKGROUND OF THE INVENTION

1. Field of the Invention

This application relates to an instrument for applying surgical clips to body tissue, and more particularly to instruments for applying surgical clips for anastomoses of a blood vessel in conventional surgical procedures and in endoscopic or laparoscopic surgical procedures.

2. Discussion of the Prior Art

The term "anastomosis" covers a variety of procedures in which blood vessels such as veins and arteries, or other tubular members, such as parts of the colon, intestines, stomach, etc., are joined or reconnected. These vessels may be joined in a variety of relative orientations, including end-to-end and end-to-side. Solid tubular structures such as peripheral nerves can also be joined together, as well as solid structures such as subcutaneous tissue and skin.

The recent advances made in the field of microsurgery has led to the development of alternatives to conventional suturing processes of joining vessels in order to accommodate the minute size of the vessels, nerves and tissues being joined during microsurgical procedures. These alternatives have also been developed with an eye towards preventing thrombosis which tends to occur at the points of penetration of the needle and sutures.

An alternative to suturing is the use of surgical clips which are applied along the juncture between the vessels or tissue portions which are to be joined, and the clips perform a holding function similar to that of sutures, but without penetrating the vessel walls or the surface of the tissue portions. Two such non-penetrating clips are shown in U.S. Pat. Nos. 4,586,503 and 4,733,664 to Kirsch et al. The former patent discloses a surgical microclip formed of plastically deformable metal or plastic material having minimal springback when crimped. The clip has a pair of parallel curved legs joined by a bridge at one end and terminating in rounded tips at the other end. The clip grips the edges of adjacent and everted tissue by crimping the legs together. The latter patent discloses a vascular surgical clip comprising a plastically deformable body portion, a tang for deforming the body, and a neck connecting the tang to the body. The body is designed to deform upon application to the tang of a predetermined tensile force, and the neck is designed to break upon application of a force in excess of the predetermined force to the tang.

As described in the above patents, the non-penetrating clips are applied over opposed edges of the vessels, the edges first being everted, or turned outward, to form flanges that are gripped between the jaws of the clips. Eversion not only enables the clip jaws to better grip the vessels, but also insures that only the interior surfaces of the vessels are in contact.

Vascular microsurgical clips are typically applied with a small hand-held tool that enables the surgeon to precisely place the clip over the tissue edges, and then to close the clip, as by applying a squeezing pressure to the tool. One example of a prior art clip applier for use in vascular microsurgery is disclosed in both U.S. Pat. Nos. 4,733,664 and 4,929,240 to Kirsch et al. These patents disclose a tool for applying a surgical clip, the tool including means for gripping and applying tension to the tang of the clip while also having means for simultaneously pushing against shoulders on the clip body. The tool disclosed in these patents requires that a clip be reloaded into the clip applier after each clip is fired, which is disadvantageous in that the vessels being repaired need to be returned to their intended function as quickly as possible, particularly blood vessels.

The need therefore exists for an instrument for applying such a surgical clip which can be utilized for vascular anastomosis. One specific need is for an instrument that can hold a plurality of clips and automatically feed and apply the clips individually to the vessel. It would be beneficial for the instrument to permit operation at various orientations with respect to the longitudinal axis of the instrument, such as through the provision of a rotation knob to rotate the body portion of the instrument. The instrument needs to be simple to manufacture, easy to manipulate and capable of applying clips with consistent accuracy so as to provide a secure joining of vessels and tissue. Since the instrument is intended to apply clips during vascular anastomosis it would be desirable to configure it similarly to other vascular surgical devices, i.e. tweezers or pincer-like implements, which are held between the thumb and forefinger of the user.

SUMMARY

The present application discloses an instrument for applying a surgical clip to a blood vessel during a microsurgical anastomosis procedure. The clip applier is designed for storage of multiple clips, and individual, automatic feed of the clips into the jaws of the instrument. Further, the applier is designed to be similar in design to other instruments used during vascular surgical procedures, i.e., to be like a tweezer or other pincer-like implement at the handle end.

The present device provides a surgical clip applier for use in vascular anastomosis surgical procedures. The instrument includes a handle housing from which extends an elongated body portion which terminates in the jaw assembly for applying the vascular clips. The handle housing includes a pair of handle members which extend from the handle housing so that they may be operated in a tweezer or pincer-like manner. The handle members are secured and are pivotable about a pivot point located at a proximally positioned point of the handle housing so that the handle members extend in a distal direction. The elongated body portion includes a slidable channel member which is operable to close the jaw members about a clip to crimp the clip at the surgical site.

The elongated body portion of the vascular clip applier includes the channel assembly, the jaw mechanism and a plurality of clips which are positioned on the jaw assembly and are maintained in place by a clip cover which serves to position the jaw assembly in the elongated body portion. A jaw clamp extending at least partially about the jaw assembly and clip cover may be provided to maintain the clip cover and jaw assembly in abutting relation to prevent relative movement between the clip cover and the jaw assembly which may result in misalignment of the series of clips being fed along the jaw assembly. The clips are advanced by a pusher member which is urged in a distal direction by a spring biased rod which passes from the handle member into the elongated body portion. In a preferred embodiment, the elongated body portion may be rotated through the provision of a rotatable knob member which is secured to the distal end of the handle housing.

The channel assembly is advanced in a distal direction to close the jaw members about a clip positioned between the jaw members through the provision of a cam link assembly which is actuated by the handle members as they are closed in the tweezer-like manner. A distal end of the cam link member is secured to the channel assembly in such a manner so as to permit rotational movement of the entire elongated body portion as well as translational or longitudinal movement of the channel assembly in the distal direction to crimp a clip positioned within the jaw assembly. The cam link assembly includes a pair of angled slots which are secured to the handle members so that as the handles are squeezed, the cam link assembly is driven in a distal direction to move the channel assembly in a distal direction towards the jaw members. Alternately, the cam link assembly may include a pair of angled cam surfaces that are engaged by a respective abutment members formed integrally with the handle members so that as the handle members are squeezed, the cam link assembly is driven in the distal direction to move the channel assembly in the distal direction toward the jaw member. When the handles are released, a compression spring returns the cam link assembly to its at rest position, thus opening the handles to return them to the ready position.

The applicator may further include an engagement surface movable into contact with the abutment surface to limit distal advancement of the channel assembly.

The individual jaw members of the jaw assembly are preferably angled with respect to the longitudinal axis at an angle of approximately 30°. The jaws each include a clip feed surface which allows a clip to ride into the clip holder portion of the jaw members under tension so as to maintain a clip in the jaws until the jaws are closed about the clip. Preferably, the clips are arranged consecutively in end-to-end fashion, and the entire series of clips are urged forward by the pusher member which is spring biased by a feed spring positioned in the handle housing. Alternatively, the clips may be provided in a stacked configuration in alignment with the longitudinal axis and fed to the jaws by a clip feed mechanism.

The housing may include a first housing half-section including a tab member and a second housing half-section including a retaining member. The tab member is movable about the retaining member to provide a snap-fit connection between the first and second housing half sections.

The vascular clip applier may also be provided with an indicator which permits the surgeon to know when the series of clips has been exhausted. In a preferred embodiment, the indicator is positioned at the proximal end of the pusher bar and will appear in a window in the clip cover or in the channel assembly to give a visual indication of the number of clips present in the instrument.

BRIEF DESCRIPTION OF THE DRAWINGS

Various preferred embodiments are described herein with reference to the drawings, wherein:

FIG. 1 illustrates a perspective view of a first embodiment of the vascular clip applying instrument;

FIG. 2 illustrates a top plan view of the instrument of FIG. 1;

FIG. 3 illustrates a side plan view of the instrument of FIG. 1;

FIG. 5 illustrates a cross-sectional top plan view of the instrument of FIG. 2, having the top half of the housing removed;

FIG. 6 illustrates the instrument of FIG. 5 in the actuated position;

FIG. 14 illustrates a partial, exploded perspective view of the keyway connection assembly of the elongated body portion and the rotation knob assembly of the instrument of FIG. 1;

FIG. 17 illustrates a perspective view of an alternate embodiment of the vascular clip applying instrument;

FIG. 25 illustrates a top plan view of the proximal portion of the instrument of FIG. 17 in the preactuated position having a portion of top housing half-section cut away;

FIG. 26 illustrates a top plan view of the proximal portion of the instrument of FIG. 17 in the actuated position having a portion of top housing half-section cut away;

FIG. 31 illustrates a side partial cutaway view of the elongated body portion of the instrument of FIG. 17 with the jaw members positioned about vasculature and the channel assembly in a retracted position;

FIG. 32 illustrates a top plan view of the distal end of the elongated body portion of the instrument of FIG. 27 with the jaw members positioned about vasculature and the channel assembly in a retracted position;

FIG. 33 illustrates a side partial cutaway view of the elongated body portion of the instrument of FIG. 17 with the jaw members positioned about vasculature and with the channel assembly in a distal position;

FIG. 34 illustrates a top plan view of the distal end of the elongated body portion of the instrument of FIG. 27 with the jaw members positioned about vasculature and the channel assembly in a distal position.

DETAILED DESCRIPTION OF THE PREFERRED EMBODIMENT

Figure 4:
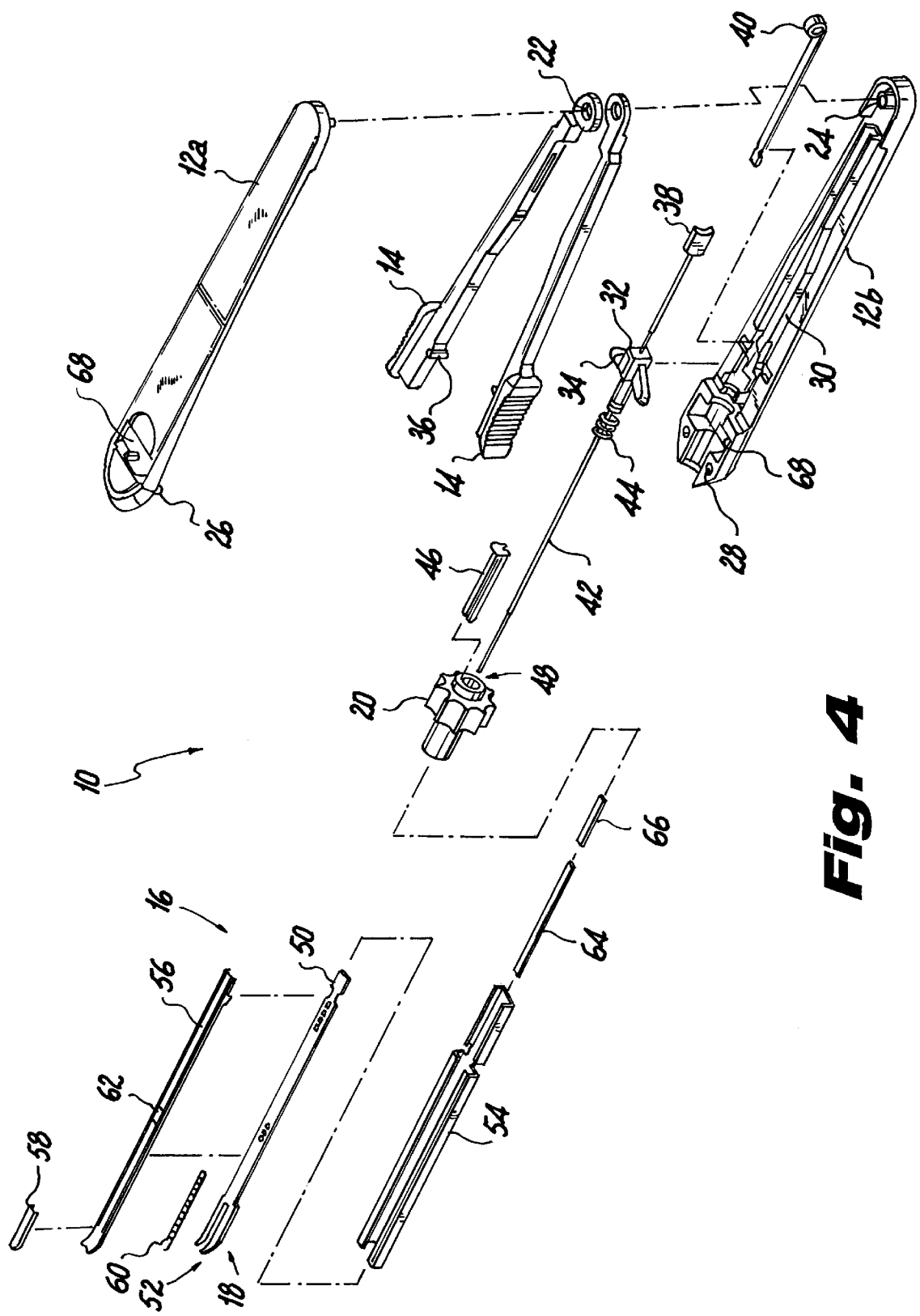
FIG. 4 illustrates an exploded perspective view of the instrument of FIG. 1.

Referring now to the drawings, in which like reference numerals identify similar or identical elements throughout the several views, and referring to the embodiment of FIGS. 1–16, and in particular to FIGS. 1–3, the vascular clip applier shown generally as 10 includes a handle housing 12 formed from a pair of housing halves 12A and 12B secured together in a conventional manner. The handle housing 12 encloses a pair of handle members 14 which are pivotable about a pivot point at the proximalmost point of the handle housing 12 as will be described below. An elongated body portion 16 extends from the handle housing 12 and terminates in a jaw assembly 18 for crimping clips upon actuation of the handle members 14. A rotation knob 20 may be provided to permit variable orientation of the jaw assembly at the surgical site to permit the surgeon to apply clips in any orientation with respect to the longitudinal axis of the instrument. As best seen in FIGS. 2 and 3, the instrument is streamlined for ease of handling and permits the surgeon to operate the instrument by closing the handles in a tweezer or pincer-like manner.

Figure 15A:
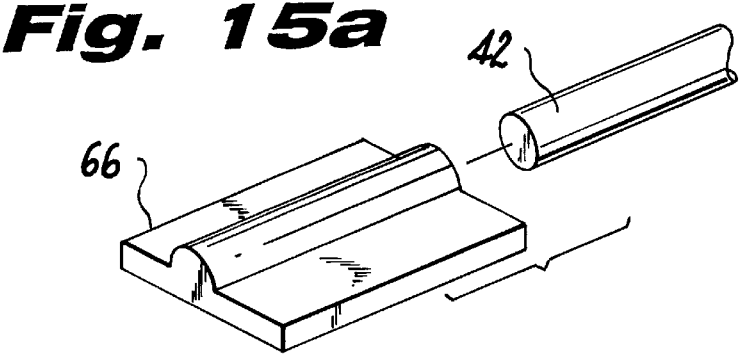
FIG. 15A illustrates a partial perspective view of the indicator member of the clip applier of FIG. 1.
Figure 15B:
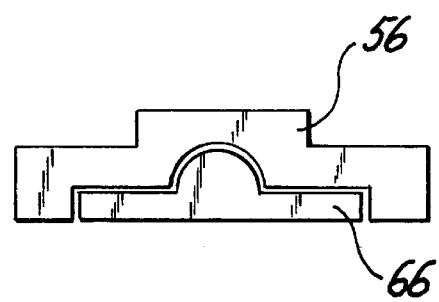
FIG. 15B illustrates a cross-section taken along lines 15B—15B of FIG. 1 showing the positioning of the indicator member within the clip cover of the elongated body portion of the instrument of FIG. 1.

Referring now to FIG. 4, there is illustrated an exploded perspective view of the instrument 10 showing the various components which comprise the instrument. With reference to the handle housing 12, it is seen that the handle members 14 include pivot holes 22 which are positioned about a pivot post 24 on the handle housing halves 12A and 12B. Pivot post 24, along with post members 26, which fit into holes 28, secure the housing in a snapfit-type arrangement, although other suitable means for securing the handle halves together in a conventional manner is acceptable. The handle housing halves 12A and 12B include boss members 30 which facilitate assembly of the components positioned within handle housing 12, and define a path of travel for several of the components within the handle portion. Located within the handle housing 12 is cam link 32, which serves to advance the channel assembly to close the jaw members towards each other to crimp a clip positioned therebetween, as will be described below. Cam link 32 includes a pair of angled slots 34, into which fit pins 36 of handle members 14, so that as handle members 14 are closed, pins 36 ride within slots 34 to drive the cam link 32 in a distal direction. Releasing the handles 14, as will be described below, permits compression spring 44 to drive cam link 32 in a proximal direction, retracting channel assembly 54 from the jaw assembly to open the jaw members to permit the next clip in the series of clips to be fed between the jaw members. The feeding process is accomplished by feed spring 40 which urges spring guide 38 in a distal direction to advance pusher rod 42, which extends through cam link 32, rotation knob 20 and into the elongated body portion 16. As seen in FIG. 15A, pusher rod 42 abuts against indicator 66, to urge indicator 66 in the distal direction. Referring again to FIG. 4, indicator 66 abuts a proximal end of pusher nose 64, which in turn abuts against the series of clips 60 to urge the clips in a distal direction and into position between the jaw members. FIG. 15B shows the positioning of the indicator with respect to the clip cover 62, as will be described below.

As stated above, elongated body portion 16 extends from the distal end of handle housing 12 and includes channel assembly 54 and clip cover 56 with jaw assembly 50 positioned therebetween. Located on jaw assembly 50 is clip series 60 and pusher nose 64, along with indicator 66. A support member 58 may be provided at the distal end of clip cover 56 for added strength.

Figure 12:
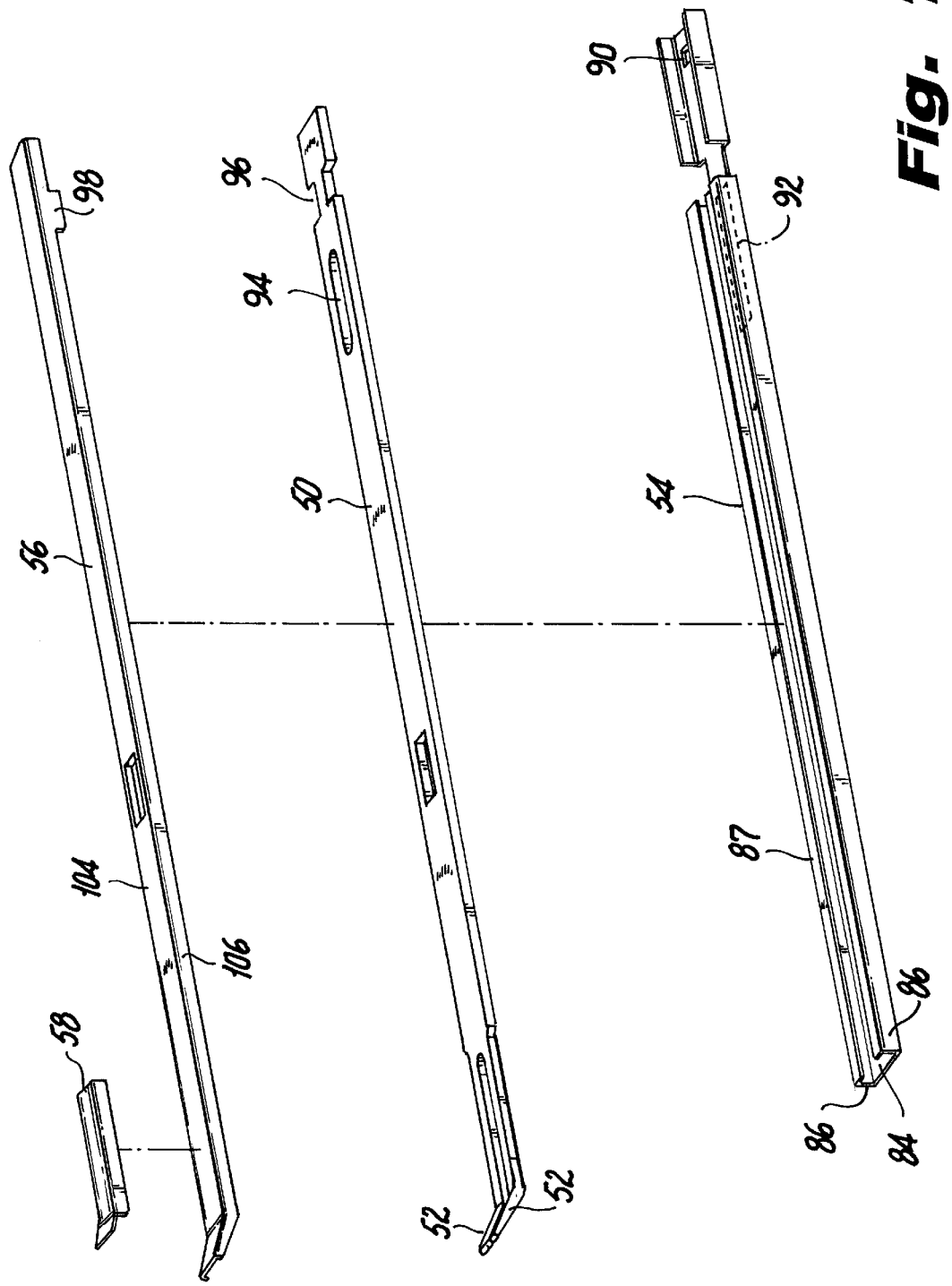
FIG. 12 illustrates an exploded perspective view of the components of the elongated body portion of the instrument of FIG. 1.

Referring now to FIG. 12, the elongated body portion 16, as stated above, includes channel assembly 54 and clip cover 56, along with jaw assembly 50 positioned therebetween. Channel assembly 54 includes a bottom wall 84 and a pair of upstanding side walls 86 which include an inturned edge 87 for capturing and securing the jaw assembly 50 and the clip cover 56. The proximalmost end of channel assembly 54 includes cam link connection slot 90 and keyway slot 92, which will be described below. Jaw assembly 50 includes a pair of jaw members 52 and further includes at its proximal end keyway slot 94 and alignment notch 96. Clip cover 56 includes a top wall 104 and a pair of depending side walls 106, each of which include an alignment tab 98. During assembly, the series of clips is positioned on clip cover 56 along with pusher nose 64 and indicator 66, and the jaw assembly 50 is located within channel assembly 54. The jaw assembly 50 is then positioned on clip cover 56 so that alignment tab 98 is positioned in alignment with alignment notch 96 to maintain alignment of jaw assembly 50 and clip cover 56. Support member 58 may also be provided at the distal end of clip cover 56 to strengthen the cover and prevent deviation during the crimping process.

Figure 13:
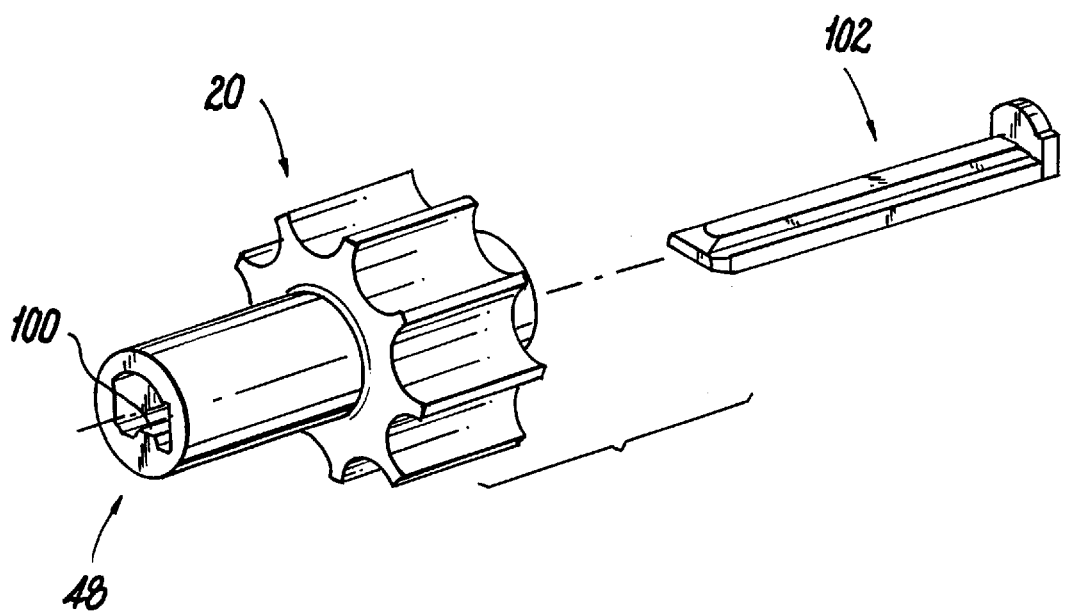
FIG. 13 illustrates an exploded perspective view of the components of the rotation knob assembly of the instrument of FIG. 1.

Referring now to FIGS. 13 and 14, after the elongated body portion 16 is assembled as described above with respect to FIG. 12, the proximalmost end of the elongated body portion 16 is positioned within the rotation knob cavity 48 of rotation knob 20. As seen in FIG. 14, when the jaw assembly 50 is assembled on channel assembly 54, keyway slot 94 and keyway slot 92 are in alignment. This permits the keyway slots 92 and 94 to align with keyway tab 100 of the rotation knob 20 so that keyway tab 100 extends upwardly through the keyway slots 92 and 94. In this position, the proximalmost end of the channel assembly 54 extends through locking knob 20 so that connector slot 90 is exposed on the proximal side of rotation knob 20. The function of this slot will be discussed below. Once the keyway tab 100 is positioned in the keyway slots 92 and 94, wedge member 102 is inserted into rotation knob 20 from the proximal side to lock the elongated body portion 16 within the cavity of rotation knob 26 by applying a downward force (with respect to FIG. 13) so that the keyway slots 92 and 94 are secured on keyway tab 100. As can be seen in FIG. 14, keyway tab 100 has substantially identical dimensions to keyway slot 94 of jaw assembly 50 so that the jaw assembly 50 may not move in a longitudinal direction with respect to the longitudinal axis of the instrument. However, as also seen in FIG. 14, keyway slot 92 of channel assembly 54, while having a side-to-side dimension which is substantially identical to the side-to-side dimension of keyway tab 100, has a longitudinal dimension which is greater than the longitudinal length of keyway tab 100. This permits the translational movement of channel assembly 54 when the handle members 14 are opened and closed to permit the crimping function.

Referring now to FIGS. 5 and 6, and also with reference to FIG. 4, the operation of the cam link assembly with respect to the handle and channel assembly will now be described. FIG. 5 illustrates the handle in the at rest position, wherein the cam link assembly 32 is biased towards the proximal direction by compression spring 44, and handles 14 are biased outwardly due to the positioning of the pins 36 in the slots 34 as shown. Cam link 32 includes cam link extension 74 which terminates in cam link connector 76. Cam link connector 76 is positioned within connector slot 90 of channel assembly 54, and permits the rotational movement of channel assembly 54 when rotation knob 20 is rotated. In addition, cam link connector 76, by being located in connector slot 90, permits the translational or longitudinal movement of the cam channel 54 when the handles are closed.

Figures 7, 8:
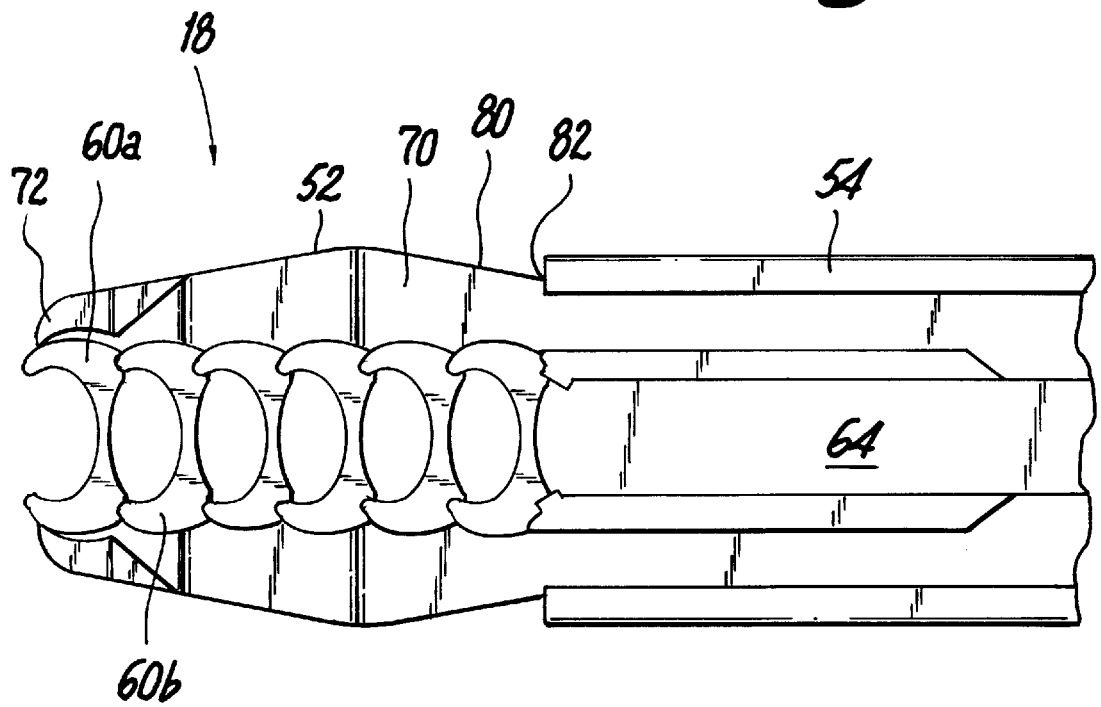
FIG. 7 illustrates a top plan view of the jaw assembly at the distal end of the vascular clip applying instrument.
FIG. 8 illustrates a partial perspective view of the distal end of the jaw mechanism.

As seen in FIGS. 5 and 6, compression spring 44 biases the cam link assembly 32 in the proximal direction, which in turn draws channel assembly 54 proximally. When the handles are closed in the direction of arrows "A", pins 36 ride within slots 34 to move cam link assembly 32 in a distal direction against the biasing of compression spring 44. This in turn drives the channel assembly 54 in a distal direction, so that the distal end of the channel assembly engages the jaw cam surface 80 of jaw assembly 50 at the channel bearing surface 82, as best seen in FIG. 7. Once the clip is positioned and crimped about the everted ends of the vascular tissue sample 78, the handles are released and compression spring 44 moves the cam link assembly 32 in a proximal direction, thus retracting channel assembly 54 and permitting the jaw members 52 to open. As this occurs, the feed spring 40 urges spring guide 38 in a distal direction, which in turn urges pusher rod 42 distally. Pusher rod 42 terminates at indicator 66, which abuts pusher nose 64, which in turn feeds the next clip 60B to the jaw assembly, as seen in FIG. 7.

Figure 16A:
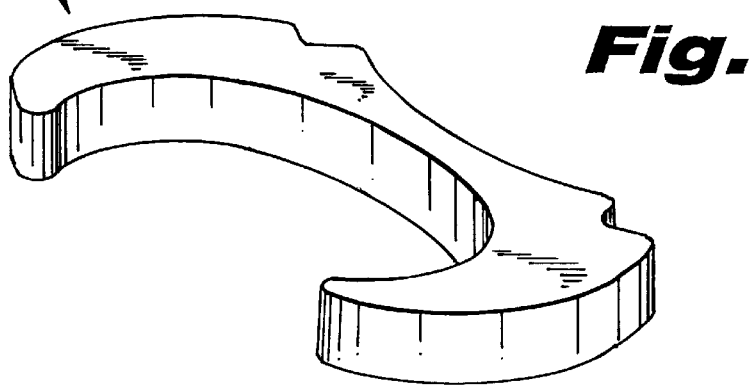
FIGS. 16A and 16B illustrate a perspective view and a top plan view, respectively, of a clip for use with the instrument of FIG. 1.
Figure 16B:
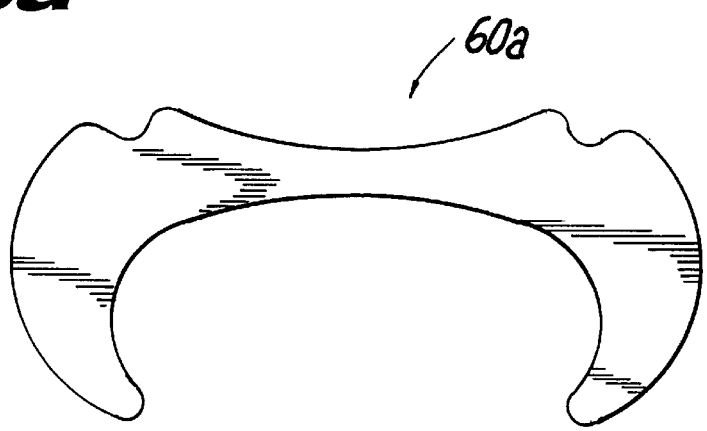

In a preferred embodiment, the jaw assembly, as best seen in FIG. 8, includes a pair of jaw members 52 which are angled with respect to the longitudinal axis at an angle of approximately 30°. The jaws have at their distalmost end clip holders 72 having an arcuate face, 72a, whose lateral separation distance is slightly less than the distance between the two legs of the clip. This permits the clip to be held between the clip holders 72 so that a clip will not fall out of the jaw assembly. As seen in FIG. 8, clip feed surface 70 permits the clips to be gently urged into the clip holders 72 under the biasing of pusher nose 64. The relatively flat face 72b forms the clips. An exemplary clip for use with the instrument 10 is shown in FIGS. 16A and 16B.

Figure 9:
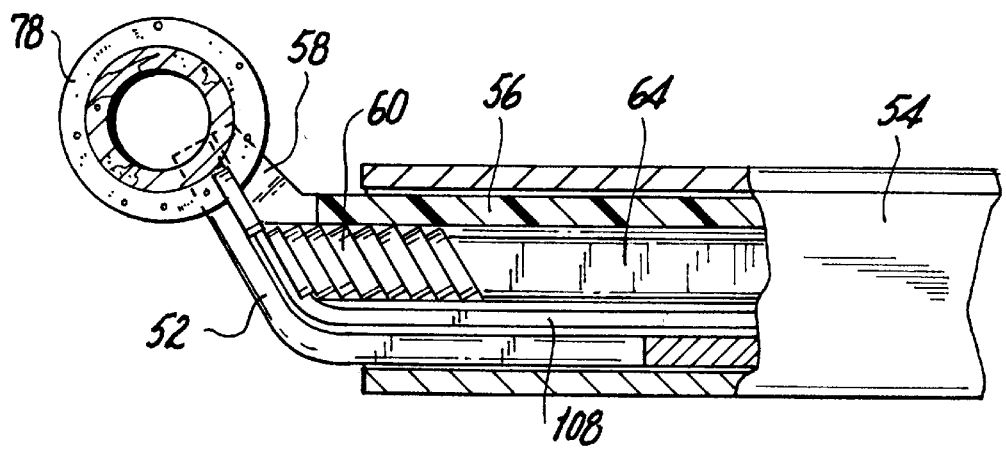
FIGS. 9–11 illustrate an alternate clip feed mechanism of the instrument of FIG. 1.
Figure 10:
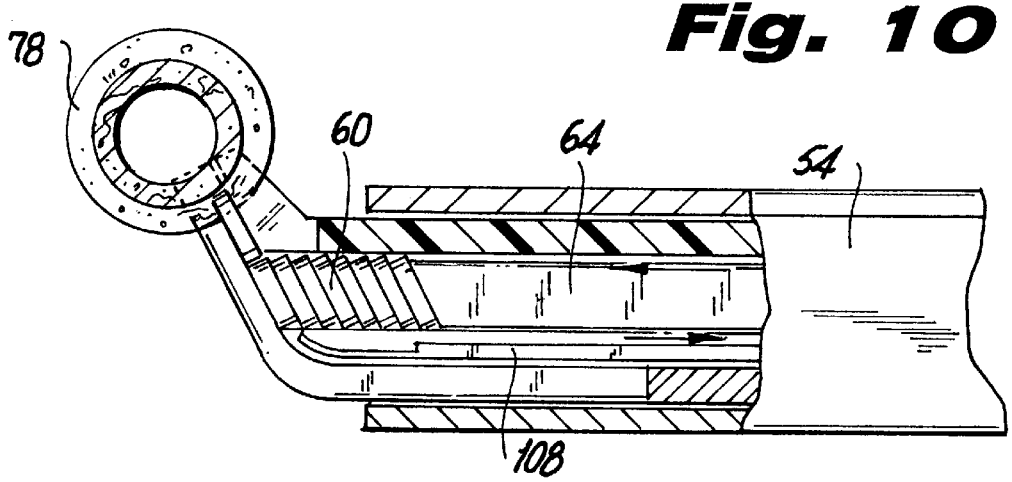
Figure 11:
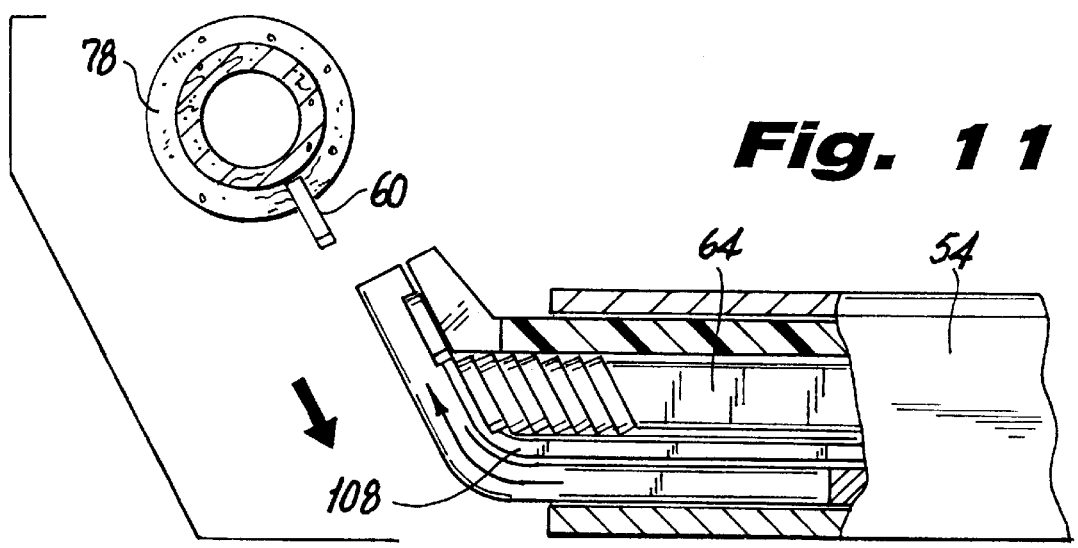

FIGS. 9–11 illustrate an alternate clip feed arrangement for the instrument 10. As seen in FIGS. 9–11, the series of clips are stacked on top of each other instead of in the sequential end-to-end arrangement of FIG. 7. The pusher nose 64 is modified to engage the proximalmost clip to urge the series of clips in a distal direction. Jaw members 52 are angled as shown, at approximately the same angle that the clips are maintained in the distal end of the instrument. In this embodiment, a clip feed bar 108 is provided, which is associated with the handle mechanism and the cam link assembly. As the handles are closed, and the jaws are crimped towards each other in the manner described above, the feed bar 108 moves in a proximal direction to a position behind the secondmost clip in the series. As the jaws are opened to release the clip which is now crimped about the tissue, the feed bar moves distally to advance the next clip into position between the jaws.

In operation, the instrument is preferably provided with a clip loaded between the jaw members for use by the surgeon so that the initial closure of the handle members crimps the clip that is positioned therebetween. Once the handles are opened, the compression spring 44 moves the cam link assembly in a proximal direction to retract the channel assembly 54, and the pusher nose 64 urges the row of clips distally so that the next clip in the series is positioned between the jaw members for the subsequent use.

An alternate embodiment of the clip applier will now be described with reference to FIGS. 17–30. FIG. 17 illustrates a vascular clip applier shown generally as 200. Briefly, clip applier 200 includes a handle housing 212 having a pair of housing half-sections 212A and 212B. A pair of handle members 214 are pivotally mounted about pivot points within the housing 212 as will be described below. An elongated body portion 216 extends distally from the housing 212 and terminates in a jaw assembly 218 for crimping is clips upon actuation of the handle members 214. A rotation knob 220 may be provided to rotate body portion 216 to permit a surgeon to vary the orientation of the jaw assembly 218 at the surgical site. The clip applier 200 is streamlined for ease of handling and may be operated by closing the handles 214 in a tweezer or pincer-like manner.

Figure 18:
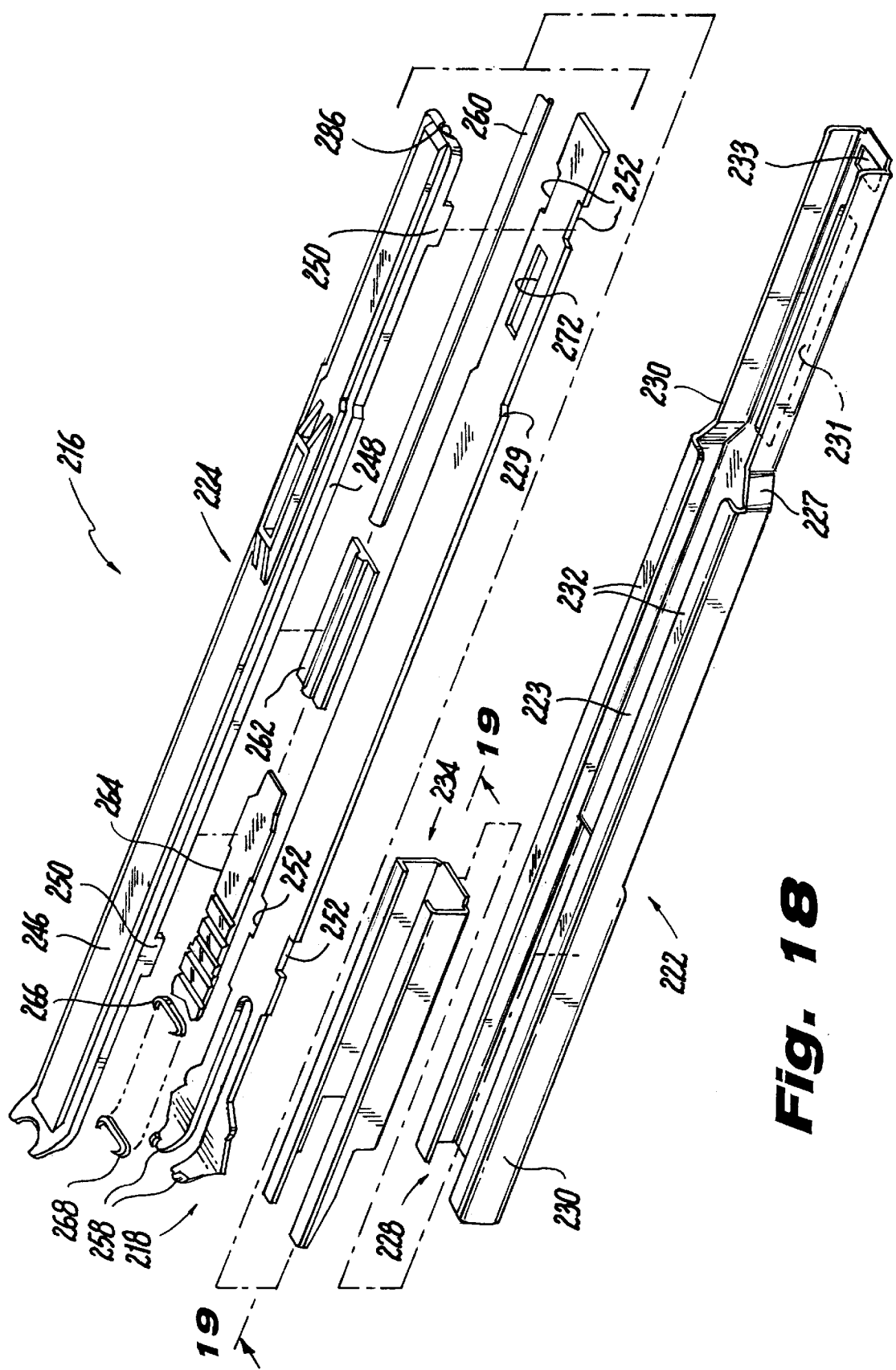
FIG. 18 illustrates an exploded perspective view of the components of the elongated body portion of the instrument of FIG. 17.

Referring to FIG. 18, the elongated body portion 216 includes a channel assembly 222, a clip cover 224, a jaw clamp 234 and a jaw assembly 218. The channel assembly 222 has a bottom wall 228 and a pair of upstanding sidewalls 230 having inturned edges 232, which together define a passageway 223 dimensioned to slidably receive clip cover 224, jaw clamp 234, and jaw assembly 218. The proximal end of channel assembly 222 has a transversely tapered transition region 227 leading to a reduced width portion 225. The proximal end of the channel assembly 222 also includes a keyway slot 231 and a connector slot 233 which will be discussed in detail below.

The central portion of the channel assembly 222 is formed with a vertically tapered transition region 235 with the distal end of passageway 223 of the channel assembly 222 having a greater height than the proximal end of the passageway 223. The distal end of passageway 223 is configured to receive the jaw clamp 234 which will be discussed in further detail hereinbelow.

Figure 19:
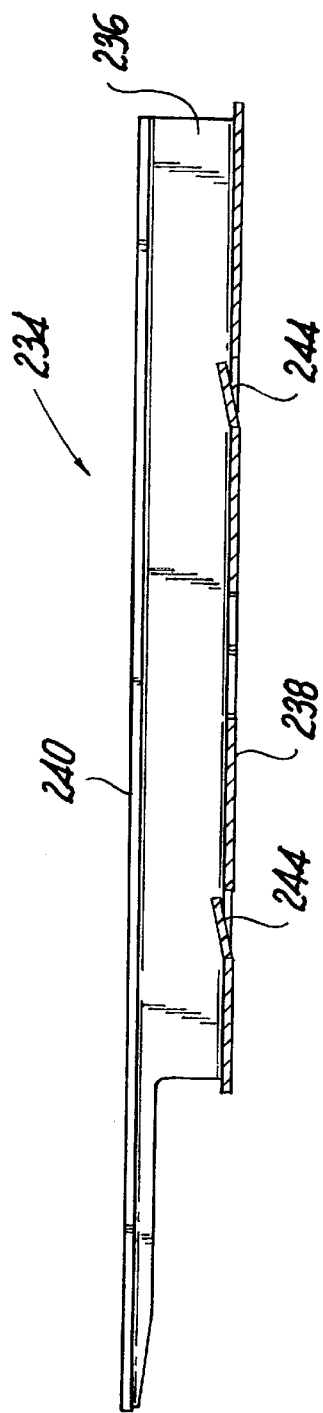
FIG. 19 illustrates a side cross-sectional view of the jaw clamp of the instrument of FIG. 17 taken along lines 19—19 of FIG. 18.
Figure 20:
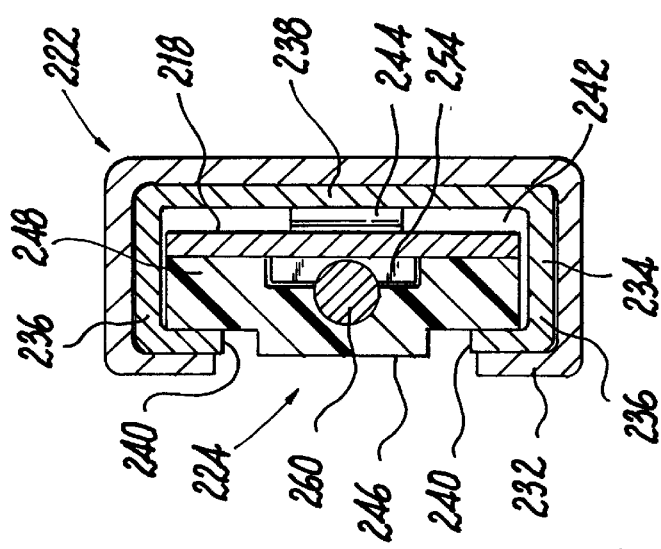
FIG. 20 illustrates a cross-sectional view taken along lines 20—20 of FIG. 17 showing the positioning of the channel assembly, the jaw clamp, the clip cover, and the jaw assembly.
Figure 21:
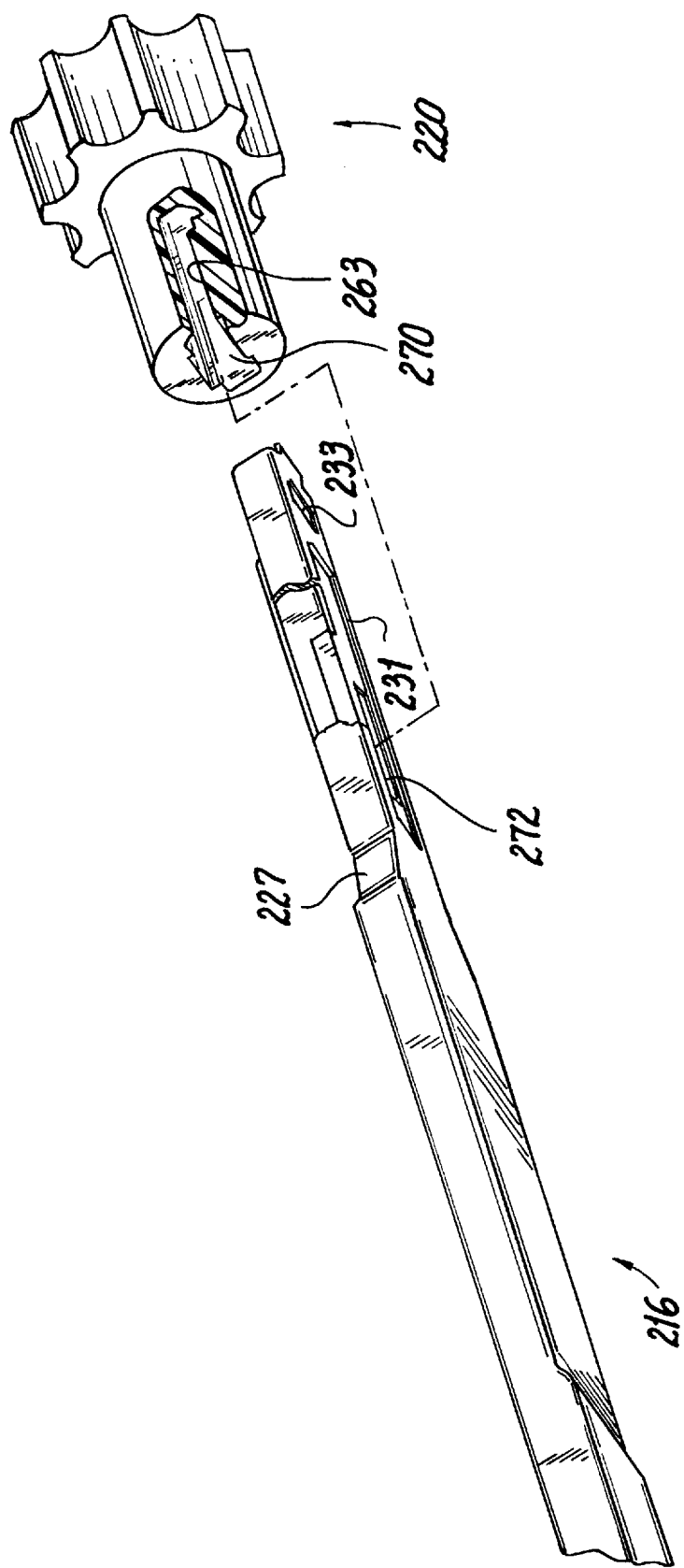
FIG. 21 illustrates a partial cross-sectional exploded perspective view of the proximal end of the elongated body portion and the rotation knob of FIG. 17.

The clip cover 224 and the jaw assembly 218 are maintained in fixed relation by the jaw clamp 234. As illustrated in FIGS. 19 and 20, the jaw clamp 234 includes a bottom wall 238 and a pair of upstanding sidewalls 236 which have inturned edges 240. The jaw clamp 234 defines an inner channel 242 which receives the jaw assembly 218 and the clip cover 224 to form the jaw clamp assembly. The inturned edges 240 of the jaw clamp 234 retain the jaw assembly 218 and clip cover 224 within the inner channel 242 and prevent their separation. The outer surface of the jaw clamp 234 is dimensioned to be received within the distal end of the channel assembly 222 and is retained therein by inturned edges 232 of channel assembly 222. A pair of resilient tabs 244 extend from bottom wall 238 of jaw clamp 234 into channel 242. The tabs 244 are positioned to engage the lower surface of the jaw assembly 218 to bias the jaw assembly 218 into abutting relation with the clip cover 224.

The clip cover 224 includes a top wall 246 and a pair of sidewalls 248 as shown in FIGS. 18 and 20. Locking tabs 250 extend downwardly from each sidewall 248 and are configured to be received in locking notches 252 formed in the jaw assembly 218. The locking tabs 250 and locking notches 252 prevent relative longitudinal movement between the jaw assembly 218 and the clip cover 224 in the assembled condition of the clip applier 200.

The clip cover 224 and jaw assembly 218 which remain stationary during operation of the clip applier 200 define a clip track 254 that extends through the elongated body portion 216 to a pair of jaw members 258 located at the distal end of the jaw assembly 218. The jaw members 258 are substantially identical to the jaw members 52 of clip applier 10 and will not be discussed in further detail herein. (See FIG. 8). A series of clips 256 is positioned on the jaw assembly 218 in head-to-tail alignment and urged by a feed mechanism distally along clip track 254 towards the jaw members 258. The feed mechanism includes an advance pusher rod 260 which abuts against the proximal end of a clip indicator 262 to urge the indicator 262 in the distal direction. The indicator 262 abuts the proximal end of pusher nose 264 to urge pusher nose 264 into engagement with the proximal-most clip 266 of the series of clips 256 to advance the series of clips 256 distally and position the distal-most clip 268 of the series of clips between the jaw members 258. The pusher rod 260 is urged distally by a biasing mechanism located within the handle housing 212 which is described below.

FIGS. 21–24 illustrate the interconnection of elongated body portion 216 and rotation knob 220. Rotation knob 220 is provided with a central bore 270 having a stepped keyway tab 263 projecting inwardly from a peripheral wall of central bore 270. The stepped keyway tab 263 is configured to engage keyway slot 231 of channel assembly 222 and a keyway slot 272 formed in the proximal end of the jaw assembly 218. The keyway slot 272 has a longitudinal dimension substantially identical to that of keyway tab 263 such that the position of the jaw assembly 218 is fixed with respect to the position of the rotation knob 220 when keyway tab 263 is engaged with keyway slot 272. Keyway slot 231 of channel assembly 222 has a longitudinal dimension greater than the longitudinal dimension of keyway tab 263, such that when keyway tab 263 is engaged in keyway slot 231, the channel assembly 222 may be moved longitudinally with respect to the rotation knob 220.

FIGS. 25 and 26 illustrate a cutaway view of the handle housing 212 showing the internal components of the device 200. The biasing mechanism for urging the advance pusher rod 260 distally is positioned within the housing and includes a feed spring 280 and a spring guide 282. (similar to FIG. 4). The spring guide 282 is urged distally into abutment with a proximal end of pusher rod 260 to urge pusher rod 260 distally. Pusher rod 260 extends through a cam link assembly 284, the rotation knob 220, and an opening 286 formed in clip cover 224 (FIG. 18) into engagement with clip indicator 262 to urge the clip indicator 262 in the distal direction. Preferably, feed spring 260 is a torsion spring, although other known biasing members may be used.

Referring temporarily back to FIG. 18, optionally a clip indicator 262 can be provided which is movable within handle housing 212 beneath a window 288 formed in clip cover 224 to provide visual indication of the number of clips remaining within the clip applier 200. For example, the clip indicator 262 may be color coded or include inscriptions to indicate the number of clips remaining within clip applier 200. Alternately, the clip cover 224 can be clear and therefore a window need not be provided.

Figure 22:
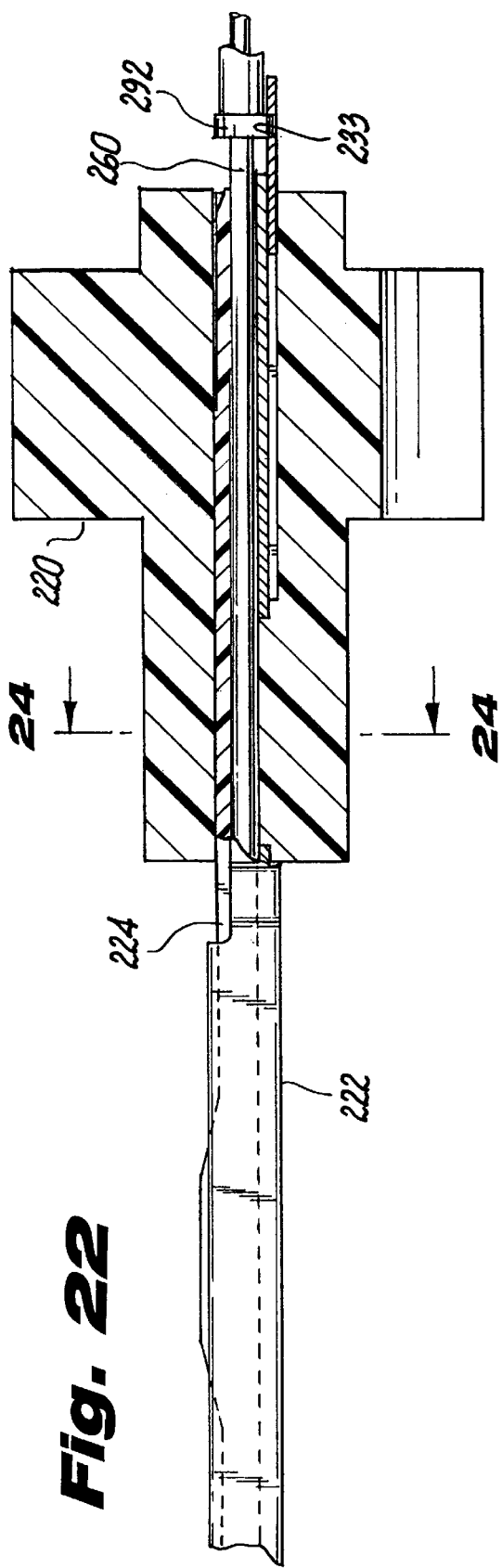
FIG. 22 illustrates a side partial cross-sectional view of the rotation knob, the distal end of the cam link assembly, and the proximal end of the elongated body portion of the instrument of FIG. 17 with the channel assembly in a retracted position.
Figure 23:
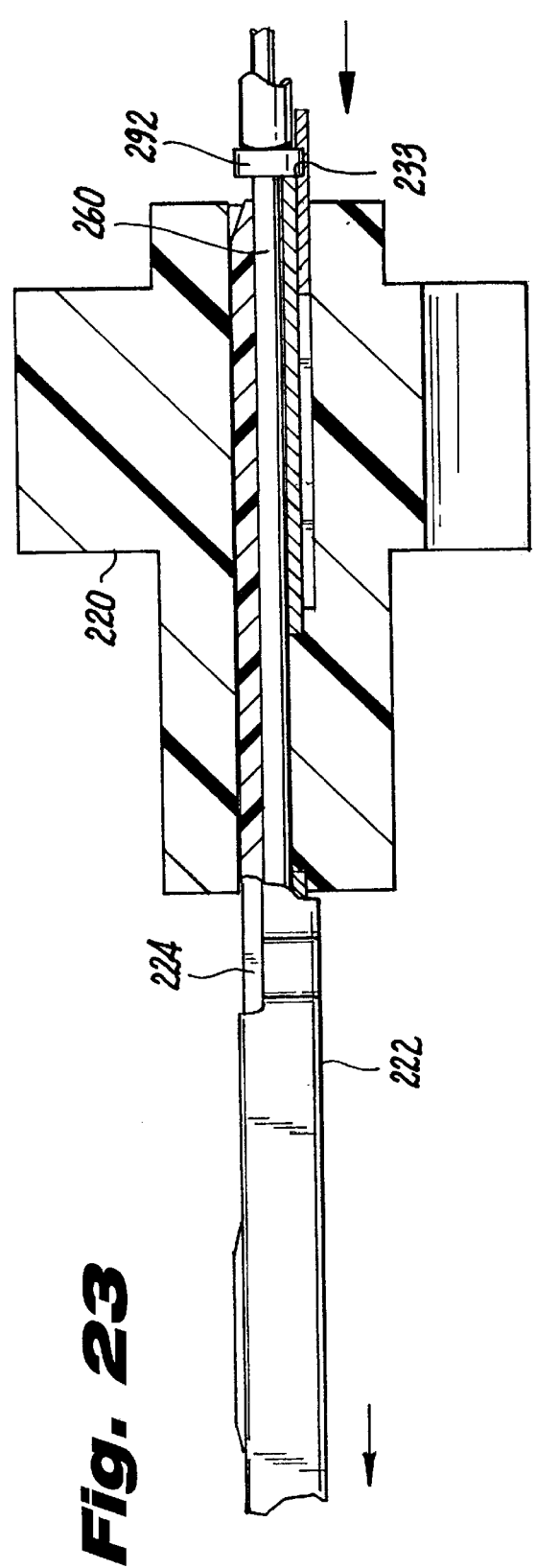
FIG. 23 illustrates a side partial cross-sectional view of the rotation knob, the distal end of the cam link assembly, and the proximal end of the elongated body portion of the instrument of FIG. 17 with the channel assembly in a distal position.
Figure 24:
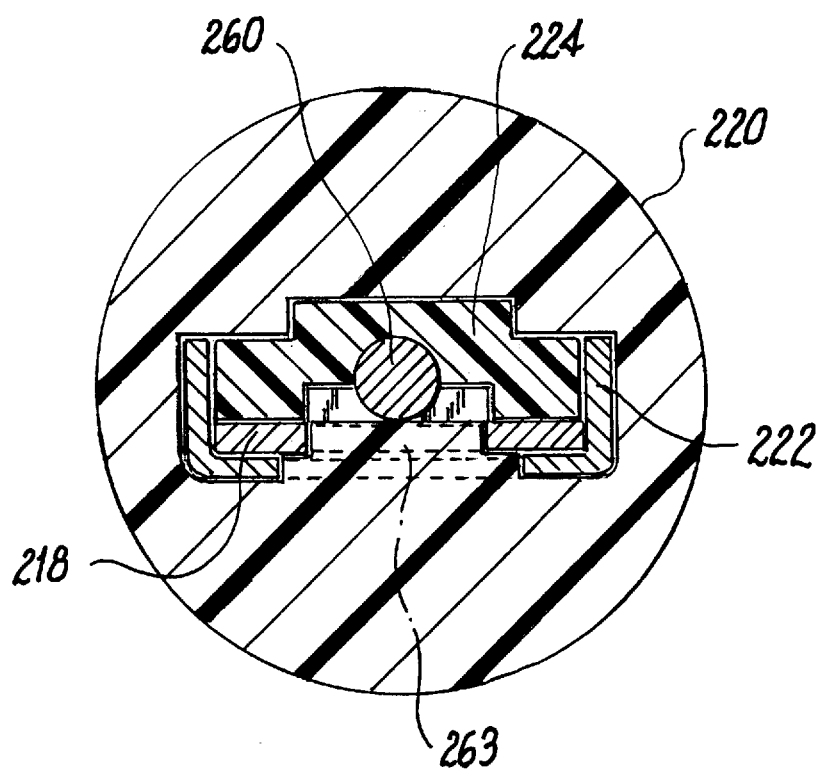
FIG. 24 illustrates a cross-sectional view taken along lines 24—24 of FIG. 22 showing the interconnection of the rotation knob and the elongated body portion.

Referring again to FIGS. 25 and 26, and also to FIGS. 22 and 23, cam link assembly 284 is slidable within handle housing 212 and includes cam surfaces 284a and 284b, and a distally extending cylindrical portion 290. The cylindrical portion 290 is formed with an annular projection 292 (FIG. 22) that is received within connector slot 233 formed in the proximal end of channel assembly 222. The annular projection 292, which may be in the form of a washer, permits rotation of channel assembly 222 in response to rotation of rotation knob 220 and translation of channel assembly 222 in response to translation of cam link assembly 284. The annular projection 292 has an engagement surface 231 that engages the proximal end 229 of jaw assembly 218 to limit distal movement of the channel assembly 218.

The handle members 214 are pivotable about pivot pins 295 and 297 into engagement with the cam link assembly 284 to cause translation of the cam link assembly 284 distally. Each handle member 214 has an abutment member 299 that engages a respective cam surface 284a and 284b to move the cam link assembly 284 distally when handle members 214 are moved in the direction indicated by arrow "B". A compression spring 294 is positioned to bias cam link assembly 284 proximally to retract the channel assembly 222 and return the handle members 214 to a preactuated condition.

Figure 27:
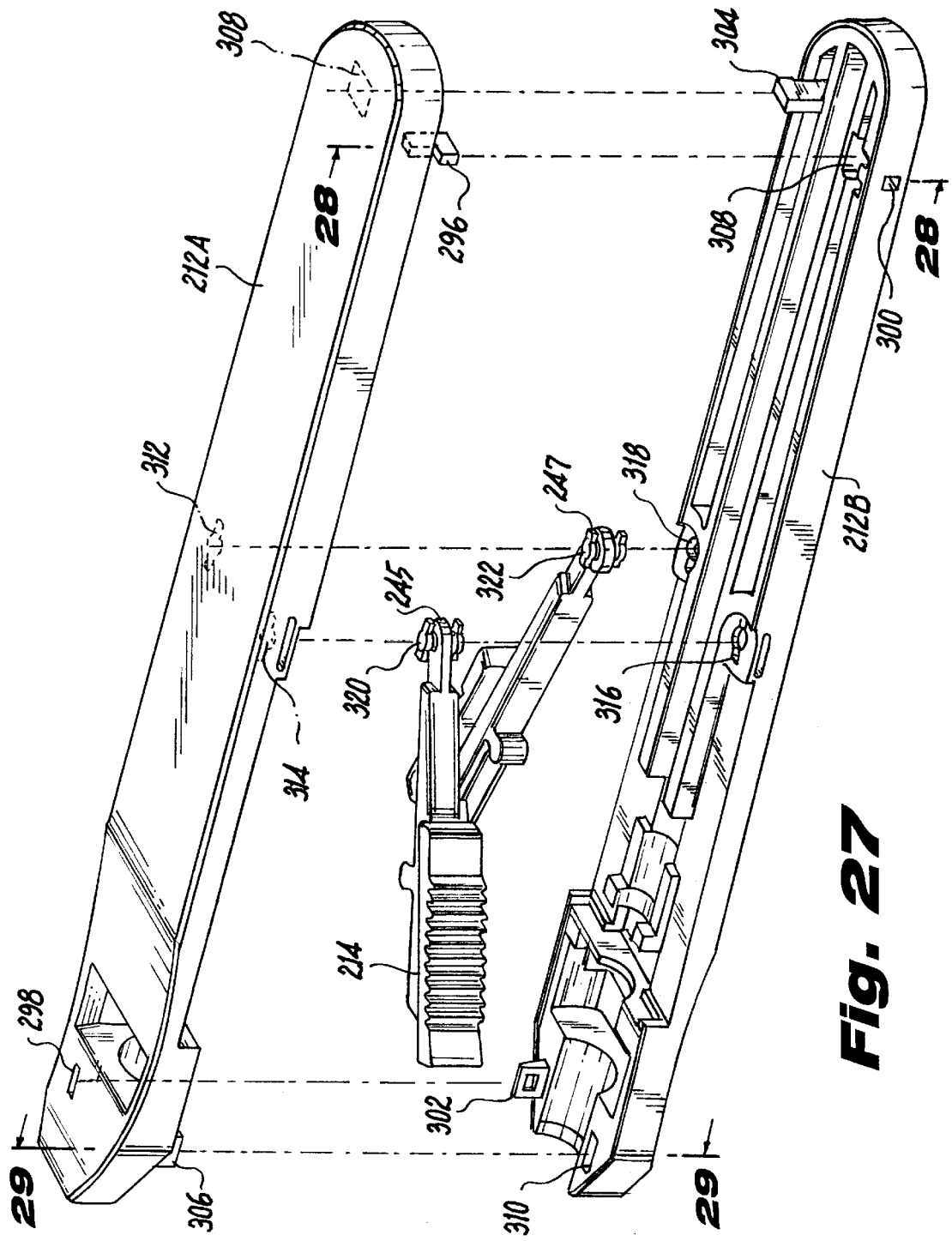
FIG. 27 illustrates an exploded perspective view of the housing half-sections and the handle members of the instrument of FIG. 17.
Figures 28, 29:
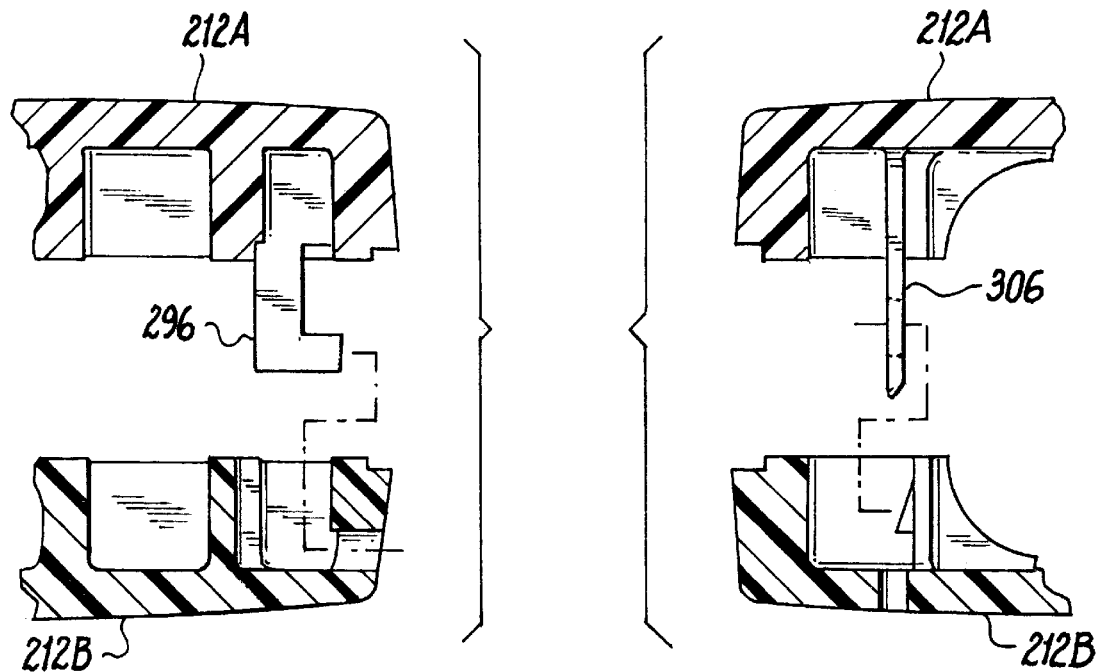
FIG. 28 illustrates a partial cross-sectional view of the proximal end of the housing half-sections taken along lines 28—28 of FIG. 27.
FIG. 29 illustrates a partial cross-sectional view of the distal end of the housing half-sections taken along lines 29—29 of FIG. 27.

Referring to FIGS. 27–29, the housing half-sections 212A and 212B may be molded from plastic material and have a snap-fit and/or an interlocking body design. For example, in a preferred embodiment a hook 296 extends from the proximal end of each housing half-section 212A and 212B. Each hook 296 is configured to be received in a respective opening 300 formed in the opposing housing half-section to provide interlocking closure of the proximal end of the housing 212. A flexible tab 306 is provided on the end of each housing half-section 212A and 212B. Each tab 306 is configured to be received in a respective slot 298 formed in the opposing housing half-section. A retaining member 304 positioned within each slot 298 has a tapered surface 305 that engages and deflects tab 306 as tab 306 is slid into slot 298 to provide snap fit closure of the distal end of the housing 212.

The central portion of the housing half-sections 212A and 212B are joined together by a keyed connection assembly including a first pair of keyed slots 312 and 314 formed on housing half-section 212A, a second pair of keyed slots 316 and 318 formed on housing half-section 212B, and a pair of rotatable key members 320 and 322. Preferably, rotatable key members 320 and 322 are formed integrally with handle member pivot pins 295 and 297, although the parts may be separately constructed and positioned. To join the central portions of housing half-sections 212A and 212B, key members 320 and 322 are positioned in the respective keyed slots 312–318 and rotated.

Figure 30:
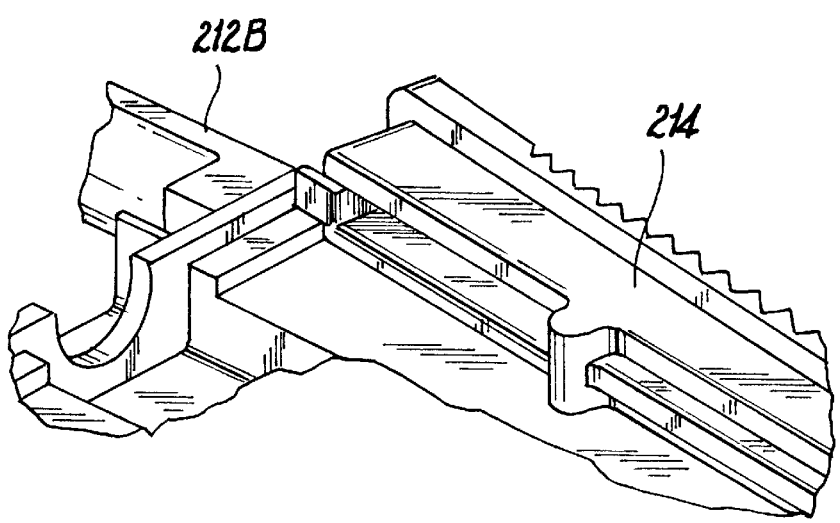
FIG. 30 illustrates a partial perspective view of the proximal end of the handle member positioned on a housing half-section of FIG. 27.

As illustrated in FIG. 30, the proximal end of each handle member 214 is provided with an extension 332. Each extension 332 is positioned between a pair of planar shelves 330 (only one is shown) formed on the housing half-sections 212A and 212B. The shelves 332 restrict the handle members to pivoting motion in a single plane.

FIGS. 25, 31, and 32 illustrate clip applier 200 in a preactuated position. Compression spring 294 has urged cam link assembly 284 proximally to move channel assembly 218, via annular projection 292 (FIG. 22) proximally to a retracted position. Handle members 214 have been rotated away from housing 212 by engagement of cam surfaces 284a and 284b of cam link assembly 284 with abutment members 300 of handle members 214. The jaw members 258 are in the open position with the distal-most clip 268 positioned between the jaw members 258.

Referring now to FIGS. 26, 33 and 34, with the open end of the jaw assembly 218 positioned about the everted ends 326 and 328 of the tissue to be joined, handle members 214 are pressed inwardly in the direction indicated by arrow "B" to move abutment members 300 inwardly against cam surfaces 284a and 284b. The cam link assembly 284 is advanced distally compressing spring 294 and moving channel assembly 222 distally as indicted by arrow "C". The distal end of the channel assembly 222 engages jaw cam surface 330 to deflect the jaw members 258 inwardly in the direction indicated by arrow "D" to crimp the distal-most clip 268 positioned between the jaw members 258 about everted ends 326 and 328 of the tissue being joined. Upon release of handle members 214, compression spring 294 urges cam link assembly 284 proximally.

It will be understood that various modifications may be made to the embodiments disclosed herein. For example, the rotatable key members of the housing connection assembly may be constructed separately from the handle member pivot pins. Therefore, the above description should not be construed as limiting, but merely as exemplifications of preferred embodiments. Those skilled in the art will envision other modifications within the scope and spirit of the claims appended hereto.

What is claimed is:

1. A surgical clip applicator comprising:
   a housing;
   a handle assembly pivotally connected to the housing;
   a jaw assembly extending distally from the housing, the jaw assembly being movable from an open position to a closed position;
   a channel assembly movable into operable engagement with the jaw assembly to move the jaw assembly from the open to the closed position;
   a clip cover extending distally from the housing, the clip cover being aligned with the jaw assembly and defining a clip track with the jaw assembly;
   a series of clips positioned along the clip track;
   a clip pusher bar movable along the clip track; and
   a jaw clamp extending at least partially about the jaw assembly and clip cover and adapted to maintain the jaw assembly and clip cover in abutting relation.

2. A surgical clip applicator as defined in claim 1, wherein the jaw clamp includes at least one resilient tab positioned to bias the jaw assembly and clip cover into abutting relation.

3. A surgical clip applicator as defined in claim 1, wherein the channel assembly is slidably mounted with respect to the housing and jaw assembly and the clip cover and the jaw clamp are longitudinally fixed with respect to the housing.

4. A surgical clip applicator as defined in claim 3 wherein the channel assembly defines a passage, the jaw assembly, clip cover, and jaw clamp forming a clamp assembly and being positioned within the passage such that the channel assembly is movable about the clamp assembly into engagement with the jaw assembly.

5. A surgical clip applicator as defined in claim 4 wherein the jaw assembly includes a stop surface and the channel assembly includes a reduced width portion, the stop surface being positioned to engage the reduced width portion to limit movement of the channel assembly about the clamp assembly.

6. A surgical clip applicator comprising:
   a housing;
   a jaw assembly extending distally from the housing, the jaw assembly being movable from an open position to a closed position;
   a channel assembly movable into operable engagement with the jaw assembly to move the jaw assembly from the open to the closed position;
   a cam link member positioned within the housing and operably connected to the channel assembly, the cam link member having a pair of cam surfaces about its periphery;
   a pair of handle members pivotally connected to the housing, each handle member having an abutment member, each abutment member being slidable along a respective one of the cam surfaces to cause the cam link member and the channel assembly to move distally to move the jaw assembly from the open to the closed position.

7. A surgical clip applicator as defined in claim 6 wherein the housing includes first and second housing half-sections, the first and second housing half-sections being snap-fit together.

8. A surgical clip applicator as defined in claim 7 wherein the first housing half-section includes a flexible tab member and the second housing half-section includes a retaining member, the tab member being movable about the retaining member to fasten the housing half-sections together.

9. A surgical clip applicator as defined in claim 8 further including a hook member provided on one of the housing half-sections and an opening configured to receive the hook member provided on the other of the housing half-sections, the hook member being engageable in the opening to interlock the housing half-sections together.

10. A surgical clip applicator as defined in claim 8 further comprising a pair of key members, wherein the central portion of the first and second housing half-sections each include a pair of key slots, each key member being engageable in one key slot of each pair of key slots in the first and second housing half-sections to fasten the first and second housing half-sections together.

11. A surgical clip applicator as defined in claim 10 wherein the handle members are pivotable about pivot pins extending between the first and second housing half-sections, the key members being formed integrally with the pivot pins.

12. A surgical clip applicator comprising:
   a housing having first and second housing half-sections;
   a handle assembly having a pair of handle members pivotably supported between the housing half-sections;
   a jaw assembly extending distally from the housing, the jaw assembly being movable from an open position to a closed position;

a series of clips positioned within the housing;

a pusher bar movable with respect to the jaw assembly;

a pair of key members formed integrally with the handle members, wherein the first and second housing half-sections each include a pair of key slots, each key member being engageable in one key slot of each pair of key slots in the first and second housing half-sections to fasten the first and second housing half-sections together;

wherein the first housing half-section includes a tab member and the second housing half-section includes a retaining member, the tab member being movable about the retaining member to provide a snap-fit connection between the first and second housing half-sections.

13. A surgical clip applicator as defined in claim 12 further including a hook member provided on one of the housing half-sections and an opening configured to receive the hook member provided on the other of the housing half-sections, the hook member being engageable in the opening to interlock the housing half-sections together.

14. A surgical clip applicator as defined in claim 12, wherein the handle members are pivotable about pivot pins extending between the first and second housing half-sections, the key members being formed integrally with the pivot pins.

15. A surgical clip applicator comprising:

a housing;

a pair of handle members pivotally connected to the housing;

a jaw assembly having a pair of jaw members, the jaw assembly being longitudinally fixed and extending distally from the housing, the jaw assembly having an abutment surface spaced proximally of the jaw members;

a channel assembly longitudinally slidable with respect to the housing; the channel assembly being movable into operable engagement with the jaw members to move the jaw members from an open to a closed position, the applicator further including an engagement surface, the engagement surface being moveable into contact with the abutment surface to limit distal advancement of the channel assembly, the engagement surface being positioned within the housing at the point of contact with the abutment surface.

16. A surgical clip applicator as defined in claim 15, wherein the channel assembly is slidably position about the jaw assembly.

17. A surgical clip applicator as defined in claim 15, further comprising an actuation mechanism, the actuation mechanism being operably connected to the channel assembly to move the channel assembly between proximal and distal positions, the engagement surface being formed on the actuation mechanism.

18. A surgical clip applicator as defined in claim 17, wherein the actuation mechanism includes a cam link assembly having a distally extending cylindrical portion, the engagement surface being formed on a distal face of the cam link assembly.

19. A surgical clip applicator as defined in claim 18, wherein the cam link assembly is connected to the channel assembly to permit relative rotation.

20. A surgical clip applicator comprising:

a housing having first and second housing half sections, wherein the first housing half-section includes a tab member and the second housing half-section includes a retaining member, the tab member being movable about the retaining member to provide a snap-fit connection between the first and second housing half-sections;

a jaw assembly extending distally from the housing, the jaw assembly having a pair of jaw members movable from an open position to a closed position, the jaw assembly being longitudinally fixed and extending distally from the housing and having an abutment surface spaced proximally of the jaw members;

a channel assembly longitudinally slidable and movable into operable engagement with the jaw assembly to move the jaw members from the open to the closed position, the applicator further including an engagement surface movable into contact with the abutment surface to limit distal advancement of the channel assembly;

a cam link member positioned within the housing and operably connected to the channel assembly, the cam link member having a pair of cam surfaces about its periphery;

a clip cover extending distally from the housing, the clip cover being aligned with the jaw assembly and defining a clip track with the jaw assembly;

a series of clips positioned along the clip track;

a clip pusher bar movable along the clip track;

a pair of handle members pivotally connected to the housing, each handle member having an abutment member which engages the cam surfaces to cause the cam link member and the channel assembly to move distally to move the jaw members from the open to the closed position; and a jaw clamp extending at least partially about the jaw assembly and clip cover and adapted to maintain the jaw assembly and clip cover in abutting relation.

\* \* \* \* \*